US008188310B2

(12) United States Patent
Cremer et al.

(10) Patent No.: US 8,188,310 B2
(45) Date of Patent: *May 29, 2012

(54) PROCESS FOR THE LONG-TERM OPERATION OF A HETEROGENEOUSLY CATALYZED PARTIAL GAS PHASE OXIDATION OF AN ORGANIC STARTING COMPOUND

(75) Inventors: Ulrich Cremer, Mannheim (DE);
Martin Dieterle, Ludwigshafen (DE);
Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/950,514

(22) Filed: Nov. 19, 2010

(65) Prior Publication Data

US 2011/0065953 A1     Mar. 17, 2011

Related U.S. Application Data

(63) Continuation of application No. 11/614,375, filed on Dec. 21, 2006, now Pat. No. 7,884,238.

(60) Provisional application No. 60/759,557, filed on Jan. 18, 2006.

(30) Foreign Application Priority Data

Jan. 18, 2006  (EP) .................................... 06100535

(51) Int. Cl.
*C07C 51/16* (2006.01)
(52) U.S. Cl. ........................ 562/545; 562/532
(58) Field of Classification Search .................. 562/532, 562/545
See application file for complete search history.

(56) References Cited

U.S. PATENT DOCUMENTS

| | | | |
|---|---|---|---|
| 3,147,084 A | 9/1964 | Franzen et al. |
| 3,702,259 A | 11/1972 | Nielsen |
| 3,799,886 A | 3/1974 | Fellice et al. |
| 3,871,445 A | 3/1975 | Wanka et al. |
| 3,956,377 A | 5/1976 | Dolhyj et al. |
| 4,077,912 A | 3/1978 | Dolhyj et al. |
| 4,256,783 A | 3/1981 | Takada et al. |
| 4,408,079 A | 10/1983 | Merger et al. |
| 4,496,770 A | 1/1985 | Duembgen et al. |
| 5,173,468 A | 12/1992 | Boehning et al. |
| 5,221,767 A | 6/1993 | Boehning et al. |
| 5,231,226 A | 7/1993 | Hammon et al. |
| 5,264,625 A | 11/1993 | Hammon et al. |
| 5,668,077 A | 9/1997 | Klopries et al. |
| 5,734,068 A | 3/1998 | Klopries et al. |
| 5,739,391 A | 4/1998 | Ruppel et al. |
| 5,821,390 A | 10/1998 | Ruppel et al. |
| 6,252,122 B1 | 6/2001 | Tenten et al. |
| 6,395,936 B1 | 5/2002 | Arnold et al. |
| 6,403,829 B1 | 6/2002 | Unverricht et al. |
| 6,410,785 B1 | 6/2002 | Zehner et al. |
| 6,525,217 B1 | 2/2003 | Unverricht et al. |
| 6,781,017 B2 | 8/2004 | Machhammer et al. |
| 6,794,539 B2 | 9/2004 | Unverricht et al. |
| 6,858,754 B2 | 2/2005 | Borgmeier |
| 6,867,328 B2 | 3/2005 | Borgmeier et al. |
| 6,881,702 B2 | 4/2005 | Arnold et al. |
| 6,888,024 B2 | 5/2005 | Dieterle et al. |
| 6,982,347 B2 | 1/2006 | Dieterle et al. |
| 6,998,504 B1 | 2/2006 | Unverricht et al. |
| 7,005,403 B2 | 2/2006 | Borgmeier et al. |
| 7,019,176 B2 | 3/2006 | Dieterle et al. |
| 7,026,506 B2 | 4/2006 | Borgmeier et al. |
| 7,115,776 B2 | 10/2006 | Hammon et al. |
| 7,154,009 B2 | 12/2006 | Dieterle et al. |
| 7,157,597 B2 | 1/2007 | Dieterle et al. |
| 7,164,039 B2 | 1/2007 | Petzoldt et al. |
| 7,211,691 B2 | 5/2007 | Petzoldt et al. |
| 7,211,692 B2 | 5/2007 | Dieterle et al. |
| 7,214,822 B2 | 5/2007 | Borgmeier et al. |
| 7,321,058 B2 | 1/2008 | Machhammer et al. |
| 7,884,238 B2 * | 2/2011 | Cremer et al. ................ 562/532 |
| 2004/0063989 A1 | 4/2004 | Hechler et al. |
| 2004/0181083 A1 | 9/2004 | Proll et al. |
| 2004/0192963 A1 | 9/2004 | Dieterle et al. |
| 2005/0049435 A1 | 3/2005 | Ha et al. |
| 2005/0096483 A1 | 5/2005 | Dieterle et al. |
| 2006/0004227 A1 | 1/2006 | Dieterle et al. |

FOREIGN PATENT DOCUMENTS

| | | |
|---|---|---|
| DE | AS 12 54 137 | 11/1967 |
| DE | A 20 25 430 | 12/1971 |
| DE | A 22 01 528 | 1/1972 |
| DE | A 21 59 346 | 6/1972 |
| DE | A 21 06 796 | 8/1972 |
| DE | A 23 51 151 | 4/1974 |
| DE | A 25 26 238 | 1/1975 |
| DE | C 25 13 405 | 10/1976 |
| DE | C 28 30 765 | 1/1980 |
| DE | A 40 22 212 | 1/1992 |
| DE | A 41 32 263 | 4/1993 |
| DE | A 41 32 684 | 4/1993 |
| DE | 43 11 508 | 12/1994 |
| DE | A 44 31 957 | 3/1995 |
| DE | A 196 22 331 | 12/1997 |
| DE | A 199 02 562 | 7/2000 |
| DE | 00/53557 | 9/2000 |

(Continued)

OTHER PUBLICATIONS

Prof. Dr. Hans Beyer, "Lehrbuch der Organischen Chemie", 17, Auflage 1973, Hirzel Verlag Stuttgart, Seite 261.

*Primary Examiner* — Taylor Victor Oh
(74) *Attorney, Agent, or Firm* — Oblon, Spivak, McClelland, Maier & Neustadt, L.L.P.

(57) ABSTRACT

A process for the long-term operation of a heterogeneously catalyzed partial gas phase oxidation of an organic starting compound, in which the reaction gas input mixture is partially oxidized over a fixed catalyst bed which is accommodated in two successive temperature zones A, B whose temperature is changed with increasing operating time such that the initially lower temperature increases and the difference between the two temperatures decreases.

22 Claims, No Drawings

FOREIGN PATENT DOCUMENTS

| | | |
|---|---|---|
| DE | A 199 10 506 | 9/2000 |
| DE | A 199 10 508 | 9/2000 |
| DE | A 199 27 624 | 12/2000 |
| DE | A 199 46 523 | 4/2001 |
| DE | A 199 48 241 | 4/2001 |
| DE | A 199 48 246 | 4/2001 |
| DE | A 100 28 582 | 12/2001 |
| DE | A 100 46 672 | 3/2002 |
| DE | A 100 46 928 | 4/2002 |
| DE | A 100 46 957 | 4/2002 |
| DE | A 101 21 592 | 5/2002 |
| DE | A 101 31 297 | 1/2003 |
| DE | A 103 50 812 | 6/2005 |
| DE | A 103 50 822 | 6/2005 |
| DE | A 103 51 269 | 6/2005 |
| DE | A 10 2004 008 573 | 9/2005 |
| EP | A 058 927 | 9/1982 |
| EP | A 092 097 | 10/1983 |
| EP | A 253 409 | 1/1988 |
| EP | A 372 972 | 6/1990 |
| EP | A 383 224 | 8/1990 |
| EP | A 415 347 | 3/1991 |
| EP | A 471 853 | 2/1992 |
| EP | A 522 871 | 1/1993 |
| EP | A 529 853 | 3/1993 |
| EP | A 608 838 | 8/1994 |
| EP | A 614 872 | 9/1994 |
| EP | A 700 714 | 3/1996 |
| EP | A 700 893 | 3/1996 |
| EP | A 1 090 684 | 4/2001 |
| EP | A 1 097 745 | 5/2001 |
| EP | A 1 106 598 | 6/2001 |
| EP | A 1 180 508 | 2/2002 |
| GB | A 1 291 354 | 10/1972 |
| GB | A 1 464 198 | 2/1977 |
| WO | 89/07101 | 8/1989 |
| WO | 00/53558 | 9/2000 |
| WO | 00/53559 | 9/2000 |
| WO | 01/96270 | 12/2001 |
| WO | 03/053558 | 7/2003 |
| WO | 2004/007064 | 1/2004 |
| WO | 2004009525 | 1/2004 |
| WO | 2004/085362 | 10/2004 |
| WO | 2004/085363 | 10/2004 |
| WO | 2004/085365 | 10/2004 |
| WO | 2004/085367 | 10/2004 |
| WO | 2004/085369 | 10/2004 |
| WO | 2004/085370 | 10/2004 |
| WO | 2005/021149 | 3/2005 |
| WO | 2005/063673 | 7/2005 |
| WO | 2005/063674 | 7/2005 |
| WO | 2005/082517 | 9/2005 |
| WO | 2005113127 | 12/2005 |

* cited by examiner

PROCESS FOR THE LONG-TERM OPERATION OF A HETEROGENEOUSLY CATALYZED PARTIAL GAS PHASE OXIDATION OF AN ORGANIC STARTING COMPOUND

CROSS REFERENCE TO RELATED APPLICATION

This application is a continuation of U.S. application Ser. No. 11/614,375, filed on Dec. 21, 2006, now U.S. Pat. No. 7,884,238 which claims the benefit of U.S. Provisional Application No. 60/759,557, filed on Jan. 18, 2006, and which claims priority to European Application No. 06100535.1, filed on Jan. 18, 2006.

A process for the long-term operation of a heterogeneously catalyzed partial gas phase oxidation (or gas phase partial oxidation) of an organic starting compound to an organic target compound, in which a reaction gas input mixture comprising the organic starting compound and molecular oxygen is first ("initially") conducted through a freshly charged fixed catalyst bed which is installed into two spatially successive (and generally adjacent) temperature zones A, B whose temperatures $T^A$ and $T^B$ are such that the difference $\Delta T^{BA}$ between the temperature $T^B$ of the temperature zone B and the temperature $T^A$ of the temperature zone A and calculated with the higher of the two temperatures as the minuend (i.e. the lower of the two temperatures $T^B$, $T^A$ is the subtrahend) $>0°$ C., with the proviso that the reaction gas input mixture flows through temperature zones A, B in the time sequence "first A" and "then B", temperature zone A extending up to a conversion of the organic starting compound of $C^A$=from 15 to 85 mol % and the conversion of the organic starting compound increasing in temperature zone B to a value $C^B$ of $\geq 90$ mol %, and in which, with increasing operating time, in order to counteract the reduction in the quality of the fixed catalyst bed, the temperature of temperature zones A, B is then changed. When $T^B$ is the minuend, $T^A$ is the subtrahend and the difference formation to determine $\Delta T^{BA}$ is to be undertaken as follows: $\Delta T^{BA}=T^B-T^A$.

A full oxidation of an organic compound with molecular oxygen is understood here to mean that the organic compound is converted under the reactive action of molecular oxygen such that all of the carbon present in the organic compound is converted to oxides of carbon and all of the hydrogen present in the organic compound is converted to oxides of hydrogen. All different reactions of an organic compound under the reactive action of molecular oxygen are combined here as partial oxidations of an organic compound.

In particular, partial oxidations shall be understood here to mean those reactions of organic compounds with the reactive action of molecular oxygen in which the organic compound to be oxidized partially, after the reaction has ended, comprises, in chemically bonded form, at least one oxygen atom more than before the partial oxidation was carried out.

A diluent gas which behaves substantially inertly under the conditions of the heterogeneously catalyzed gas phase partial oxidation is understood to mean those diluent gases whose constituents, under the conditions of the heterogeneously catalyzed gas phase partial oxidation, each constituent viewed alone, are retained to an extent of more than 95 mol %, preferably to an extent of more than 99 mol %.

The loading of a fixed catalyst bed catalyzing a reaction step with reaction gas mixture is understood to mean the amount of reaction gas mixture in standard liters (=l (STP); the volume in liters that the appropriate amount of reaction gas mixture would take up under standard conditions, i.e. at 0° C. and 1 atm) which is fed to the fixed catalyst bed, based on the volume of its bed (pure inert material sections are not included) per hour ($\rightarrow$unit=l (STP)/l·h). The loading may also be based only on one constituent of the reaction gas mixture. In that case, it is the volume of this constituent which is fed to the fixed catalyst bed, based on the volume of its bed, per hour.

It is common knowledge that numerous commodity chemicals (target products) can be obtained by partial and heterogeneously catalyzed oxidation of a wide variety of organic starting compounds with molecular oxygen in the gas phase in a fixed catalyst bed. Examples include the conversion of propylene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 092 097, EP-A 058 927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene, p-xylene or naphthalene to phthalic anhydride (cf., for example, EP-A 522 871) or the corresponding acids, and the conversion of butadiene to maleic anhydride (cf., for example, DE-A 2106796 and DE-A 1624921), the conversion of n-butane to maleic anhydride (cf., for example, GB-A 1 464 198 and GB-A 1 291 354), the conversion of indanes to, for example, anthraquinone (cf., for example, DE-A 20 25 430), the conversion of ethylene to ethylene oxide or of propylene to propylene oxide (cf., for example, DE-B 12 54 137, DE-A 21 59 346, EP-A 372 972, WO 89/07101, DE-A 43 11 608 and Beyer, Lehrbuch der organischen Chemie [Textbook of organic chemistry], 17th edition (1973), Hirzel Verlag Stuttgart, page 261), the conversion of propylene and/or acrolein to acrylonitrile (cf., for example, the DE-A 23 51 151), the conversion of isobutene and/or methacrolein to methacrylonitrile (i.e. the term "partial oxidation" in this document shall also comprise partial ammoxidation, i.e. a partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 101 31 297, EP-A 1 090 684, EP-A 608 838, DE-A 100 46 672, EP-A 529 853, WO 01/96270 and DE-A 100 28 582), the conversion of isobutane to methacrolein and/or methacrylic acid, and the reactions of ethane to give acetic acid, of ethylene to give ethylene oxide, of benzene to phenol and of 1-butene or 2-butene to the corresponding butanediols, etc.

The fixed catalyst bed has the task of causing the desired gas phase partial oxidation to proceed preferentially over the full oxidation.

The chemical reaction proceeds when the reaction gas mixture flows through the fixed bed during the residence time of the reaction gas mixture therein.

The solid state catalysts are frequently oxide compositions or noble metals (for example Ag). The catalytically active oxide composition may, in addition to oxygen, comprise only one other element or more than one other element (in the case of so-called multielement oxide compositions).

Particularly frequently, the catalytically active oxide compositions used are those which comprise more than one metal element, especially transition metal element. In this case, reference is made to multimetal oxide compositions. Typically, they are not simple physical mixtures of oxides of their elemental constituents, but rather mixtures of complex poly compounds of these elements. In practice, the aforementioned catalytically active solid compositions are generally shaped to a wide variety of geometries (rings, solid cylinders, spheres, etc.). The shaping (to the shaped body) can be effected such that the catalytically active composition is shaped as such (for example in extruders or tableting apparatus), so that the result is a so-called unsupported catalyst, or by applying the active composition to a preshaped support (cf., for example, WO 2004/009525 and WO 2005/113127).

Examples of catalysts which are suitable for inventive heterogeneously catalyzed fixed bed gas phase partial oxidations of at least one organic starting compound can be found, for example, in DE-A 100 46 957, in EP-A 1 097 745, in DE-A 44 31 957, in DE-A 100 46 928, in DE-A 199 10 506, in DE-A 196 22 331, in DE-A 101 21 592, in EP-A 700 714, in DE-A 199 10 508, in EP-A 415 347, in EP-A 471 853 and in EP-A 700 893.

Typically, heterogeneously catalyzed gas phase partial oxidations have a highly exothermic profile. Owing to a multitude of possible parallel and side reactions, the sole measure of additional catalyst use is normally insufficient with regard to a highly selective reaction of the at least one organic starting compound to be oxidized partially to the desired target product. Instead, it is additionally necessary for a highly selective performance of a heterogeneously catalyzed gas phase partial oxidation in a fixed catalyst bed to control the profile of the reaction temperature or the profile of the temperature of the fixed catalyst bed in flow direction of the reaction mixture to a certain extent.

According to the teachings of the prior art, it has generally been found to be advantageous in this regard to install a freshly charged fixed catalyst bed in two spatially successive temperature zones A, B whose temperatures $T^A$ and $T^B$ are such that the difference $\Delta T^{BA}$ between the temperature $T^B$ of temperature zone B and the temperature $T^A$ of temperature zone A and calculated with the higher of the two temperatures as the minuend is >0° C., and to conduct the reaction gas input mixture comprising the organic starting compound and the molecular oxygen through the fixed catalyst bed such that the reaction gas input mixture flows through temperature zones A, B in the time sequence "first A" and "then B", the length of temperature zone A being such that it extends up to a conversion of the organic starting compound of $C^A$=from 15 to 85 mol % and the length of temperature zone B is such that the conversion of the organic starting compound increases in temperature zone B to a value $C^B$ of $\geq$90 mol % (cf., for example, DE-A 199 27 624, DE-A 199 48 523, WO 00/53557, DE-A 199 48 248, WO 00/53558, WO 2004/085365, WO 2004/085363, WO 2004/085367, WO 2004/085369, WO 2004/085370, WO 2004/085362, EP-A 1 159 247, EP-A 1 159 246, EP-A 1 159 248, EP-A 1 106 598, WO 2005/021149, US-A 2005/0049435, WO 2004/007064, WO 05/063673, WO 05/063674).

In practice, temperature zones A, B are generally implemented in such a way that the fixed catalyst bed is introduced into one reaction chamber (installed in one reaction chamber), around which in each case a fluid (preferably liquid) heat carrier (a heat exchange medium) is conducted or passed (in and out), for reasons of heat transfer, into two substantially separate sections A, B spatially successive (and generally adjacent) in flow direction of the reaction gas mixture, said heat carrier touching the material shell of the reaction chamber (the wall of the reaction chamber) (being in contact with it) along the particular section A or B. The heat carrier conducted within section A is normally fed with the temperature $T^A$ and the heat carrier conducted within section B is normally fed with the temperature $T^B$. The total capacity of the heat carrier stream conducted is normally very much larger than the total heat capacity of the reaction gas mixture stream conducted.

In the aforementioned prior art, and in this document too, the temperature of a temperature zone is understood to mean the temperature of the part of the fixed bed catalyst charge (of the fixed catalyst bed) disposed in the temperature zone when the process according to the invention is practised but in the theoretical absence of the chemical heat of reaction.

For example, and particularly simply from an application point of view, the fixed catalyst bed may be disposed (be installed) in the catalyst tubes (reaction tubes) of a so-called two-zone tube bundle reactor, as described, for example, in DE-A 199 10 508, 199 48 523, 199 10 506 and 199 48 241 and also in the documents WO 2004/085362, WO 2004/085370, WO 2004/085369, WO 2004/085363, WO 2004/085365, WO 2004/007064 and WO 2004/085367. A preferred variant of a two-zone tube bundle reactor usable in accordance with the invention is disclosed by DE-C 28 30 765. However, the two-zone tube bundle reactors disclosed in DE-C 25 13 405, U.S. Pat. No. 3,147,084, DE-A 22 01 528, EP-A 383 224 and DE-A 29 03 218 are suitable for a performance of the process according to the invention.

In other words, in the simplest manner, the fixed bed catalyst charge to be used in accordance with the invention is disposed in the reaction tubes of a multiple catalyst tube fixed bed reactor (tube bundle reactor) and two substantially spatially separate heating media (for example ionic liquids, water (steam), salt melts or liquid metals) are conducted (passed; in and out) around the reaction tubes. The tube section over which the particular salt bath or metal bath extends represents one temperature zone.

In addition to the above-described external measures of temperature control, the reactants are typically diluted with a gas which is substantially inert under the conditions of the heterogeneously catalyzed gas phase partial oxidation and is capable of absorbing heat of reaction released with its heat capacity (internal measure of temperature control).

The reaction gas mixture of a heterogeneously catalyzed gas phase partial oxidation of at least one organic starting compound as described at the outset will therefore, in addition to the at least one organic starting compound and molecular oxygen, generally additionally comprise at least one inert diluent gas.

One of the most frequently additionally used inert diluent gases is molecular oxygen which is always used automatically when the oxygen source used for the heterogeneously catalyzed gas phase partial oxidation is air.

Another often additionally used inert diluent gas, owing to its general availability and advantageous specific heat, is steam.

Other inert diluent gases typically used additionally are noble gases (e.g. He, Ar, Ne) or the carbon oxides $CO_2$ and/or CO.

The use of diluent gases with maximum molar heat capacity is typically particularly advantageous (cf., for example, EP-A 253 409). These include, for example in the case of a partial oxidation of an unsaturated organic starting compound, frequently saturated hydrocarbons, for example propane in the case of a partial oxidation of propylene to acrolein and/or acrylic acid.

In many cases, cycle gas is also used additionally as an inert diluent gas (cf. EP-A 1 180 508). Cycle gas refers to the residual gas which remains after a one-stage or multistage (multiple stages are generally employed when the partial oxidation of an organic starting compound to a target compound proceeds in successive steps; in these cases, it is frequently appropriate to optimize both the fixed catalyst bed and the other reaction conditions to the particular reaction step and to carry out the particular reaction step over the fixed catalyst bed which catalyzes this reaction step specifically (in a tailored manner) and is frequently installed (accommodated) in a spatially separate reactor or a spatially separate reaction section, i.e. as a or in a separate reaction stage; however, it may also be employed when, for reasons of heat removal or for other reasons (cf. DE-A 199 02 562), the conversion is spread between a plurality of reactors connected in series; one example of a heterogeneously catalyzed gas phase partial oxidation frequently carried out in two stages is the partial oxidation of propylene to acrylic acid; the propylene is partially oxidized to acrolein in the first reaction stage and acrolein to acrylic acid in the second reaction stage; in a corresponding manner, methacrylic acid preparation, usually starting from isobutene, is frequently also carried out in two stages; both aforementioned partial oxidations may also be carried out in one stage (both steps over one fixed catalyst bed installed (accommodated) in one reactor with catalyst catalyzing both steps), as described, for example, for the partial oxidation of propylene to acrylic acid in DE-A 101 21 592; in the multistage partial oxidation, the product gas mixture of the preceding stage is generally used without intermediate removal, if appropriate after addition of inert gas and/or molecular oxygen as secondary gas, and if appropriate on completion of direct and/or indirect cooling, as such to charge the next reaction stage) heterogeneously catalyzed gas phase partial oxidation of at least one organic compound when the target product has been removed more or less selectively (for example by absorption into a suitable solvent or by fractional condensation or by a superimposition of absorption and condensation) from the product gas mixture.

In general, it consists predominantly of the inert diluent gases used for the partial oxidation and also of steam typically formed as a by-product or added as a diluent gas in the partial oxidation, and carbon oxides formed by undesired full oxidation as a side reaction. It partly also comprises small amounts of molecular oxygen unconsumed in the partial oxidation (residual oxygen) and/or of unconverted organic starting compound and/or unconverted intermediate.

The inert diluent gases used additionally are, though, not only helpful in absorbing the heat of reaction but generally simultaneously ensure safe operation of the heterogeneously catalyzed gas phase partial oxidation of the organic starting compound by keeping the reaction mixture either outside the explosion range or within a region of the explosive range which is still safely controllable.

In spite of the external and internal measures described for controlling the reaction temperature or the temperature of the fixed catalyst bed, the temperatures of temperature zones A, B are normally different from the reaction temperature along the fixed catalyst bed in each case (the temperature of the reaction gas mixture in each case) or effective temperature of the fixed catalyst bed present in each case (it corresponds substantially to the reaction temperature present at the same level). The effective temperature of the fixed catalyst bed is the actual temperature of the fixed catalyst bed, which includes both the influence of the fluid heat carrier conducted outside the reaction chamber and the heat of the reaction of the partial oxidation (whereas the term "temperature of the temperature zone", as already stated, excludes the influence of the heat of reaction of the partial oxidation). The temperature of a temperature zone, in contrast to the effective temperature of the fixed catalyst bed in flow direction along it, is normally substantially constant. When the temperature of a temperature zone is not entirely constant, the term temperature of a temperature zone here means the (numerical) mean of the temperature over the temperature zone. The individual temperature zones are heated substantially independently of one another. Normally, the effective temperature of the fixed catalyst bed at the particular bed level is greater than the temperature of the accompanying temperature zone.

It is of significance in the aforementioned context that the temperature of the reaction gas mixture (and hence also the effective temperature of the fixed catalyst bed) as it passes through the fixed catalyst bed in flow direction of the reaction gas mixture, typically passes through a maximum value in the particular temperature zone or falls starting from such a maximum value (known as the hotspot value $T^{maxA}$ (in temperature zone A) or $T^{maxB}$ (in temperature zone B)). The difference between hotspot value and the temperature of the accompanying temperature zone is referred to as hotspot expansion $\Delta T^{HB}_A$ (in temperature zone A) or $\Delta T^{HB}_B$ (in temperature zone B).

One cause of this is that the reactant concentration in the reaction gas mixture at the inlet (entry) of the reaction gas mixture into the fixed catalyst bed is at a maximum, which causes particularly high reaction rates there, which is accompanied by particularly high evolution of heat of reaction per unit time (on entry into the fixed catalyst bed, the reaction gas mixture (=the reaction gas input mixture) generally has substantially the temperature of temperature zone A).

Another cause of this is the finite heat transfer from the reaction gas mixture to the heat carrier.

According to the teaching of the prior art, the general process conditions in the freshly charged fixed catalyst bed are generally selected advantageously such that $T^{maxA}-T^{maxB}$ is $\geq 0°$ C. (cf. WO 2004/085362, WO 2004/085370 and WO 2004/085363).

In addition, according to the teachings of the cited prior art, the general process conditions in the freshly charged fixed catalyst bed are normally selected such that both $\Delta T^{HB}_B$ and $\Delta T^{HB}_A$ generally do not exceed 80° C. Usually, these temperature differences are $\leq 70°$ C., frequently from 20 to 70° C., and the temperature differences are preferably low.

Moreover, in the freshly charged fixed catalyst bed, the change (preferably simultaneously) of $\Delta T^{HB}_A$ or $\Delta T^{HB}_B$, when the temperature of the accompanying temperature zone is increased by +1° C., is normally (cf. the acknowledged prior art documents) $\leq 9°$ C., preferably $\leq 7°$ C., or $\leq 5°$ C. or $\leq 3°$ C.

Usually, heterogeneously catalyzed gas phase partial oxidations for economically viable reactant conversions of the partial oxidation based on a single pass of the reaction gas mixture through the fixed catalyst bed require elevated temperatures in temperature zones A, B. In general, these are a few hundred ° C., typically from 100 to 600° C., frequently from 150 to 500° C., usually from 200 or 250 to 450° C.

The working pressure in heterogeneously catalyzed gas phase partial oxidations over the fixed catalyst bed may be below 1 atm or above 1 atm. In general, it is in the range from $\geq 1$ to 20 atm, or to 10 atm. A working pressure of 100 atm is typically not exceeded.

It is common knowledge that heterogeneously catalyzed gas phase partial oxidations of an organic starting compound to an organic target compound (to a target product), in which a reaction gas input mixture comprising the organic starting compound and molecular oxygen is conducted through a freshly charged fixed catalyst bed which is installed in two spatially successive temperature zones A, B, whose temperatures $T^A$ and $T^B$ are such that the difference $\Delta T^{BA}$ between the temperature $T^B$ of temperature zone B and the temperature $T^A$ of temperature zone A and calculated with the higher of the two temperatures as the minuend is >0° C., with the proviso that the reaction gas input mixture flows through the temperature zones A, B in the time sequence "first A" and "then B", temperature zone A extending up to a conversion of the organic starting compound of $C^A$=from 15 to 85 mol % and the conversion of the organic starting compound increasing in temperature zone B to a value $C^B$=≧90 mol %, can be operated substantially continuously over a prolonged period under substantially unchanged conditions over one and the same fixed catalyst bed.

However, the fixed catalyst bed normally loses quality with increasing operating time. In general, the volume-specific activity of the fixed catalyst bed in particular worsens (under otherwise unchanged process conditions, the reactant conversion based on single pass of the reaction gas mixture through the fixed catalyst bed decreases with increasing operating time, which reduces the intended space-time yield of target product in a production plant). The selectivity of target product formation usually also suffers.

EP-A 1 106 598 and DE-A 10351269 attempt to take account of the aforementioned development in the long-term operation of a heterogeneously catalyzed gas phase partial oxidation of an organic starting compound to be carried out advantageously as described over one and the same fixed catalyst bed by gradually increasing the temperature of the fixed catalyst bed in the course of the operating time with otherwise substantially constant operating conditions, in order to substantially retain the reactant conversion on single pass of the reaction gas mixture through the fixed catalyst bed (it is possible, as recommended, for example, by WO 2004/085369, DE-A 103 51 269, DE-A 103 50 812, DE-A 103 50 822 and EP-A 614 872, to additionally counteract the reduction in quality of the fixed catalyst bed in long-term operation by regenerating the fixed catalyst bed from time to time; to this end, the process for heterogeneously catalyzed fixed bed gas phase partial oxidation is interrupted (for example when (meth)acrylic acid polymer formed in an undesired manner in the workup section of a (meth)acrylic acid plant has to be removed and the partial oxidation also has to be interrupted in this context, or when the partial oxidation is interrupted because the reaction gas mixture has inadvertently assumed a composition which may be controllable only with difficulty from an explosion point of view) and, for example, conducting a hot mixture of molecular oxygen and inert gas through the fixed catalyst bed). Such a regeneration can also be effected according to DE-A 102004008573, or to WO 05/082517.

However, a disadvantage of the teachings of EP-A 1 106 598 and of DE-A 10351269 is that they suggest a synchronous increase in the temperature in the two temperature zones A, B. In other words, $T^A$ and $T^B$ are increased to the same extent (by just as many ° C.).

Such a procedure is advantageous over a procedure without increase of the temperature of the fixed catalyst bed and can also be employed advantageously in principle in all partial oxidation processes addressed in this document (for example especially to the processes for partial oxidation of propylene to acrolein and of acrolein to acrylic acid described in the documents WO 2004/085362, WO 2004/085370, WO 2004/085369, WO 2004/085363, WO 2004/085365 and WO 2004/085367).

However, it is disadvantageous in that, although it does ensure the retention of the desired reactant conversion (based on single pass of the reaction gas mixture through the fixed catalyst bed) under otherwise unchanged operating conditions, this is normally at the cost of decreased selectivity of target product formation.

It was therefore an object of the present invention to provide an improved process for long-term operation of a heterogeneously catalyzed gas phase partial oxidation carried out in two temperature zones as described.

Accordingly, a process has been found for the long-term operation of a heterogeneously catalyzed partial gas phase oxidation of an organic starting compound to an organic target compound, in which a reaction gas input mixture comprising the organic starting compound and molecular oxygen is first conducted through a freshly charged fixed catalyst bed which is installed into two spatially successive (and generally adjacent) temperature zones A, B whose temperatures $T^A$ and $T^B$ are such that the difference $\Delta T^{BA}$ between the temperature $T^B$ of the temperature zone B and the temperature $T^A$ of the temperature zone A and calculated with the higher of the two temperatures as the minuend >0° C., with the proviso that the reaction gas input mixture flows through temperature zones A, B in the time sequence "first A" and "then B", temperature zone A extending up to a conversion of the organic starting compound of $C^A$=from 15 to 85 mol % and the conversion of the organic starting compound increasing in temperature zone B to a value $C^B$ of ≧90 mol %, and in which, with increasing operating time, in order to counteract the reduction in the quality (in particular the reduction in the volume-specific activities) of the fixed catalyst bed, the temperature of temperature zones A, B is then changed, wherein, with increasing operating time, the temperature of that temperature zone which initially ("at the start") had the lower temperature is increased (preferably substantially constantly) and the difference $\Delta T^{BA}$ between the temperatures of the two temperature zones is reduced (preferably substantially constantly; reducing here explicitly also comprises an increasing "negative"), the difference being formed by the temperature of that temperature zone which initially had the higher temperature retaining its position as the minuend.

Above statements and all other statements on the process according to the invention in this document are valid especially for the heterogeneously catalyzed fixed bed gas phase partial oxidation of propylene to acrolein and/or acrylic acid, of isobutene to methacrolein and/or methacrylic acid, of (meth)acrolein to (meth)acrylic acid, of propane to acrolein and/or acrylic acid, and of isobutane to methacrolein and/or methacrylic acid. It will be appreciated that they are also valid for all other heterogeneously catalyzed gas phase oxidations mentioned at the outset of this document.

In the further course of this document, the process according to the invention and particular embodiments will be illustrated and detailed by way of example especially using the example of the heterogeneously catalyzed fixed bed gas phase partial oxidation of propylene to acrolein or of acrolein to acrylic acid. However, this is done without any restriction of the general validity of the present invention and is generally applicable correspondingly to the other heterogeneously catalyzed fixed bed gas phase partial oxidations mentioned in this document.

In principle, in the process according to the invention, before the inventive measure is taken (i.e. "at the start"), either $T^A$ or $T^B$ may be the smaller of the two temperatures for advantageous long-term operation (for example depending on the configuration of the freshly charged fixed catalyst bed).

Which of the two temperatures was the smaller depends not least upon at what reactant loading of the fixed catalyst bed the process for heterogeneously catalyzed fixed bed gas phase partial oxidation is carried out (it will be appreciated that the selection of the catalyst to be used is influential here too).

At relatively low reactant loadings on the fresh fixed catalyst bed, the condition $T^B-T^A<0°$ C. is frequently advantageous, while the condition $T^B-T^A>0°$ C. is normally advantageous with increasing reactant loading of the fixed catalyst bed. In principle, the difference $T^B-T^A$ for the performance of the process according to the invention over the freshly charged fixed catalyst bed will, advantageously from an application point of view, be adjusted so as to result in a value of $\geq 0°$ C. for the difference $T^{maxA}-T^{maxB}$. In general, $T^{maxA}-T^{maxB}$ for the freshly charged fixed catalyst bed will be adjusted such that this difference is not more than 80° C. Appropriately from an application point of view, $T^{maxA}-T^{maxB}$ for the freshly charged fixed catalyst bed is $\geq 3°$ C. and $\leq 70°$ C., particularly advantageously $\geq 5$ and $\leq 60°$ C., or $\leq 50°$ C. Very particularly advantageously, this difference is $\geq 5$ and $\leq 40°$ C., or $\geq 5$ and $\leq 25°$ C., or $\geq 5$ and $\leq 20°$ C., or $\leq 15°$ C. Frequently, this difference is also from $\geq 0$ to $\leq 5°$ C.

In the inventive procedure, it is then necessary, in the long-term operation of the process according to the invention over one and the same fixed catalyst bed, to increase the temperature of that temperature zone which initially had the lower temperature and to reduce the difference $\Delta T^{BA}$ between the temperatures of the two temperature zones, the difference being formed by the temperature of that temperature zone which initially had the higher temperature retaining its position as the minuend.

Under the prerequisite that the temperature of temperature zone B ($T^B$) was initially (previously, "at the start") the higher temperature, the temperature of temperature zone A ($T^A$) would be increased in long-term operation in accordance with the teaching given in this document. An accompanying decrease in the difference $\Delta T^{BA}$ can then in principle be achieved by three different operating modes:
a) the temperature of temperature zone B is likewise increased, but not as greatly as the temperature of temperature zone A;
b) the temperature of temperature zone B is retained;
c) the temperature of temperature zone B is lowered.

Under the prerequisite that the temperature of temperature zone A ($T^A$) was initially (previously) the higher temperature, the temperature of temperature zone B ($T^B$) would be increased in long-term operation in accordance with the teaching given in this document. An accompanying decrease in the difference $\Delta T^{BA}$ can then in principle be achieved by the three following operating modes:
a) the temperature of temperature zone A is likewise increased, but not as greatly as the temperature of temperature zone B;
b) the temperature of temperature zone A is retained;
c) the temperature of temperature zone A is lowered.

Especially in the case of the aforementioned operating modes b) and c), but in principle also in the case of operating mode a), it is possible that $\Delta T^{BA}$ changes its preceding sign in the course of long-term operation (compared with the value of the same parameter for fresh fixed catalyst bed) in the process according to the invention. Quite generally, the magnitude of $\Delta T^{BA}$ will generally not exceed 60° C., but usually 50° C. In other words, the magnitude $\Delta T^{BA}$ in the process according to the invention may, for example, be from $\geq 0$ to 60° C., or from $\geq 1$ to 55° C., or from $\geq 5$ to 50° C., or from $\geq 10$ to 40° C., or from $\geq 15$ to 35° C., or from $\geq 20$ to 30° C.

Advantageously in accordance with the invention, the procedure will generally be such that $\Delta T^{BA}$ does not change its preceding sign for as long as possible in long-term operation (for example within an operating time of 2 months or of 6 months, or of 12 months, or of 18 months, or of 24 months, or of 30 months, or of 36 months or more).

It should be emphasized at this point that the temperatures of temperature zones A and B ($T^A$ and $T^B$) in industrial-scale operation, for various reasons, can be subject to certain deviations (generally within the interval of $\pm 20°$ C. or $\pm 10°$ C.) (for example when an intermediate regeneration according to DE-A 10351269 is undertaken; immediately after completion of intermediate regeneration (in comparison to the operation immediately before the intermediate regeneration), lower temperatures (in individual cases, this temperature difference may even be up to 40° C. or more) of the temperature zones are generally sufficient in order to ensure the same reactant conversion based on single pass of the reaction gas mixture through the fixed catalyst bed under otherwise unchanged conditions). In this case, the actual profile of the temperature of the particular zone is plotted over time and a fitted curve is placed through the measurement points by the method of least mean squares developed by Legendre and Gauss. When the inventive features are fulfilled on the basis of these fitted curves, use is made of the inventive procedure.

In the case that, in the course of an inventive heterogeneously catalyzed gas phase partial oxidation, owing, for example, to changed market demand or boundary conditions changed in another way in the course of the long-term operation of one and the same fixed catalyst bed, boundary conditions of the process, for example the loading of the fixed catalyst bed, or the loading of the fixed catalyst bed and the reactant conversion based on single pass of the reaction gas mixture through the fixed catalyst bed (conversion of the organic starting compound) with direct recycling (such a change would also be an increase in the working pressure according to DE-A 10 2004 025 445) to the temperature of temperature zones A, B, in order subsequently to retain them changed in this way in the course of further operation over a prolonged period (operating period), an inventive procedure is present even when, in this subsequent prolonged operating period with reference to the fixed catalyst bed and its operation (substantially "immediately") after the aforementioned change, the inventive characterizing features are fulfilled as the operation of a "fresh fixed catalyst bed".

Moreover, the process of a heterogeneously catalyzed partial gas phase oxidation of an organic starting compound over the freshly charged fixed catalyst bed shall be understood to mean the performance of the process after completion of any conditioning of the fixed catalyst bed which may occur, i.e., after attainment of the quasi-steady operating state.

Quite generally, the changes of $T^A$, $T^B$ and of $\Delta T^{BA}$ to be undertaken in accordance with the invention can be undertaken in the process according to the invention such that, even in the course of the long-term operation of the fixed catalyst bed, a difference of $T^{maxA}-T^{maxB} \geq 0°$ C. is substantially retained (for example continually within the range of $\geq 0°$ C. and $\leq 80°$ C., or $\geq 1°$ C. and $\leq 70°$ C., or $\geq 2°$ C. and $\leq 60°$ C., or $\geq 3°$ C. and $\leq 50°$ C., or $\geq 4°$ C. and $\leq 40°$ C., or $\geq 5°$ C. and $\leq 30°$ C., or $\geq 5°$ C. and $\leq 25°$ C., or $\geq 5°$ C. and $\leq 20°$ C. or $\leq 15°$ C.; or else continuously within the range of $\geq 0°$ C. and $\leq 5°$ C.).

Preference is given to such an embodiment of the inventive procedure, since it causes particularly high target product selectivities. In general, it is achieved when the above-detailed operating modes c) are employed.

However, the changes of $T^A$, $T^B$ and of $\Delta T^{BA}$ to be undertaken in accordance with the invention can also be undertaken in such a way that, in the course of the long-term operation of the fixed catalyst bed, the difference $T^{maxA}-T^{maxB}$ changes from $\geq 0°$ C. to $<0°$ C. (for example from $\leq 80°$ C. to up to $-20°$ C., or up to $-10°$ C., or up to $-5°$ C., or from $\leq 60°$ C. to up to $-20°$ C., or up to $-10°$ C., or up to $-5°$ C., or from $\leq 40°$ C. or from ≦20° C. to up to −20° C., or up to −10° C., or up to −5° C., or from ≦10° C. to up to −20° C., or up to −10° C., or up to −5° C.).

Preference is likewise given to such an embodiment of the inventive procedure since it enables particularly long lifetimes (total operating times) of the fixed catalyst bed. On attainment of $T^{maxA}-T^{maxB}=-20°$ C. at the latest, the fixed catalyst bed will, however, normally be exchanged fully or at least partly for a fresh fixed catalyst bed. In general, such an embodiment is achieved when the above-detailed operating modes a) are employed, but less markedly also for the operating modes b).

However, it will be appreciated that it is also possible in the process according to the invention, advantageously in accordance with the invention, to proceed initially according to an operating mode c) (the initially (previously) lower of the two temperatures $T^A$, $T^B$ is increased (preferably substantially constantly) and the previously (initially) higher of the two temperatures $T^A$, $T^B$ is lowered (preferably substantially constantly)) and the process according to the invention in long-term operation is thus operated initially from the point of view of maximum selectivity of target product formation (under otherwise substantially unchanged process conditions such as the composition of the reaction gas input mixture, the loading of the fixed catalyst bed with organic starting compound and reaction gas mixture, and reactant conversion based on single pass of the reaction gas mixture through the fixed catalyst bed).

Subsequently, it is then possible, for the purpose of maximizing the lifetime of the fixed catalyst bed, to switch to an operating mode b) or a).

In principle, it is possible in the process according to the invention to jump between operating modes a), b) and c) as desired, provided that the features to be fulfilled in accordance with the invention are fulfilled.

Generally, use is also made of the process according to the invention by one who operates the process according to the invention only over a certain time period of the long-term operation and leaves the inventive long-term operating mode before the partial or full replacement of the fixed catalyst bed by a fresh bed.

In general, use will be made of the process according to the invention at the latest when the fixed catalyst bed is in such a state that $C^B$, under otherwise unchanged process conditions, would be at least 0.2 mol %, or at least 0.3 mol %, or at least 0.4 mol %, or at least 0.5 mol % lower than the value for $C^B$ under the same process conditions over the fresh catalyst bed.

Quite generally, $C^A$=from 15 to 85 mol % and $C^B ≧ 90$ mol % is generally retained in the long-term operation of the process according to the invention. Especially in the case of a heterogeneously catalyzed partial oxidation of propylene to acrolein or of acrolein to acrylic acid (but generally also in the case of other possible heterogeneously catalyzed gas phase partial oxidations), it is preferred when $C^B ≧ 92$ mol %, or ≧94 mol %, or ≧96 mol %. In the case of the heterogeneously catalyzed partial oxidation of acrolein to acrylic acid, $C^B$ during long-term operation is even particularly advantageously a continuous ≧98 mol %, or ≧99 mol %, in many cases even ≧99.5 or ≧99.9 mol %.

The catalysts to be used and other process conditions will otherwise, appropriately from an application point of view, be selected such that the selectivity of target product formation, based on single pass of the reaction gas mixture through the fixed catalyst bed, is ≧80 mol %, or ≧90 mol %, in many cases even ≧92 mol %, or ≧94 mol %, or ≧96 mol %.

Appropriately from an application point of view, the process according to the invention is preferably performed in the two-zone multiple catalyst tube reactors already addressed. The radial temperature gradient of the heat carrier within a temperature zone is generally from 0.01 to 5° C., frequently from 0.1 to 2° C. and is, advantageously in accordance with the invention, at a minimum.

Typically, the temperature of the heat carrier will rise by from 0 to 15° C. from when it enters the temperature zone to when it leaves the temperature zone (caused by the exothermicity of the reaction). Typically, the aforementioned ΔT will, in accordance with the invention, be from 1 to 10° C., or from 2 to 8° C., or from 3 to 6° C.

However, it can in principle also be carried out in other reactors having two temperature zones of the indirect heat exchanger type.

In general, the long-term operation of the process according to the invention will extend to at least 2 operating months, or to at least 4 operating months, or at least 6 operating months, or least 1 operating year, or at least 2 operating years and in some cases even to up to 10 operating years or more. When the values of $T^{maxA}$, $T^{maxB}$ attain the temperatures at which the thermal treatment of the catalyst precursor composition for preparing the catalyst is effected, the fixed catalyst bed will, appropriately from an application point of view, be replaced at least partly or fully by a fresh fixed catalyst bed.

With a view to the selectivity of target product formation, the reason for the advantage of the inventive procedure is presumably that it counteracts a procedure in which target product already formed in temperature zone A, within temperature zone B, has to pass through excessively high reaction temperatures which promote full combustion of the target product formed. At the same time, the inventive procedure opens up the possibility, viewed over long-term operation, of working towards fully exploiting the catalytic potential of the available fixed catalyst bed substantially over the entire fixed catalyst bed. In this context, the present invention embraces the fact that the deactivation of the fixed catalyst bed does not proceed homogeneously over the fixed catalyst bed when the process according to the invention is performed over the freshly charged fixed catalyst bed. Instead, it will proceed particularly markedly, inter alia, where $T^{maxA}$ and $T^{maxB}$ are present, which is why their position would normally be shifted naturally in flow direction of the reaction gas mixture along the fixed catalyst bed in long-term operation without inventive change in the temperature of temperature zones A, B.

Preferably in accordance with the invention, the inventive procedure will be employed in combination with an intermediate regeneration according to the teaching of DE-A 103 51 269. Moreover, a partial bed change according to the teaching of DE-A 10232748 or of WO 2004/009525 will be undertaken before the fixed catalyst bed is exchanged fully. In this case, the partial fixed catalyst bed change may in all cases extend, in flow direction of the reaction gas mixture, to up to 80%, or only to up to 70%, or only to up to 60%, or only to up to 50%, or only to up to 40%, or only to up to 30%, or preferably to up to 25%, more preferably to from 30 to 50% and most preferably to from 35 to 45% of the bed length of the particular fixed catalyst bed (a top charge consisting to an extent of 100% of inert material (the first charge from the flow point of view) is not counted as belonging to the fixed catalyst bed). In a corresponding manner, for the purposes of the present invention, a final charge consisting to an extent of 100% of inert material (the end charge from the flow point of view) is not counted as belonging to the fixed catalyst bed. However, an intermediate charge consisting to an extent of 100% of inert material will typically not be counted as belonging to the fixed catalyst bed. Appropriately, the aforementioned percentage for a partial catalyst change is frequently not less than 5%, or not less than 10% or not less than 20%.

When the process according to the invention over the freshly charged fixed catalyst bed is a heterogeneously catalyzed fixed bed gas phase partial oxidation of propylene to acrolein, the differences recommended as advantageous $T^{maxA}-T^{maxB}$ (for example $\geq 0°$ C. and $\leq 80°$ C., frequently $\geq 1°$ C. and $\leq 70°$ C., often $\geq 2°$ C. and $\leq 60°$ C., in many cases $\geq 3°$ C. and $\leq 50°$ C., advantageously $\geq 4°$ C. and $\leq 40°$ C., preferably $\geq 5°$ C. and $\leq 30°$ C., or $\leq 20°$ C., more preferably $\geq 5°$ C. and $\leq 15°$ C., or else $\geq 0°$ C. and $\leq 5°$ C.), in the case of relatively low ($\geq 80$ l (STP)/l·h and $\leq 130$ l (STP)/l·h or $\leq 110$ l (STP)/l·h) propene loadings on the fresh fixed catalyst bed, are frequently established when firstly both the temperature of temperature zone A and the temperature of temperature zone B are in the range from 290 to 380° C. and secondly the difference between the temperature of temperature zone B ($T^B$) and the temperature of temperature zone A ($T^A$), i.e. $\Delta T^{BA}=T^A-T^B$, is $>0°$ C. and $\leq 20°$ C. or $\leq 10°$ C., or $>0°$ C. and $\leq 5°$ C., or frequently $>0°$ C. and $\leq 3°$ C. (in this case, the temperature of temperature zone B in the inventive long-term operation would necessarily be increased (preferably constantly) and at least one of operating modes a) to c) applied to the temperature of temperature zone A (the whole process preferably in such a way that $T^{maxA}-T^{maxB} \geq 0°$ C. is maintained)). The temperatures of the two temperature zones A, B preferably remain within the temperature range from 290 to 380° C.

When the heterogeneously catalyzed fixed bed gas phase partial oxidation of propylene to acrolein is practised with increased propylene loadings on the fresh fixed catalyst bed ($>130$ l (STP)/l·h, or $\geq 140$ l (STP)/l·h, or $\geq 160$ l (STP)/l·h and generally $\leq 200$ or $\leq 300$ l (STP)/l·h, or normally $\leq 600$ l (STP)/l·h), the differences $T^{maxA}-T^{maxB}$ recommended as advantageous (see above) over the freshly charged fixed catalyst bed are normally established when firstly both the temperature of temperature zone A and the temperature of temperature zone B are in the range from 290 to 380° C. and secondly the difference between the temperature of temperature zone B ($T^B$) and the temperature of temperature zone A ($T^A$), i.e. $\Delta T^{BA}=T^B-T^A$, is $\geq 0°$ C. and $\leq 50°$ C., or $\geq 5°$ C. and $\leq 45°$ C., or $\geq 10°$ C. and $\leq 40°$ C., or $\geq 15°$ C. and $\leq 30°$ C., or $\leq 35°$ C. (for example 20° C. or 25° C.) (in this case, the temperature of temperature zone A in the inventive long-term operation would necessarily be increased (preferably constantly) and at least one of operating modes a) to c) applied to the temperature of temperature zone B (the whole process preferably in such a way that $T^{maxA}-T^{maxB} \geq 0°$ C. is maintained; preferably operating mode c))). The temperatures of the two temperature zones A, B preferably remain in the temperature range from 290 to 380° C.

Advantageously, the temperature of temperature zone A in an inventive heterogeneously catalyzed fixed bed gas phase partial oxidation of propylene to acrolein (irrespective of the propylene loading of the fixed catalyst bed) during the inventive long-term operation (and during the operation of the fresh charge) is advantageously within the preferred range of from 305 to 365° C. or in the more preferred range of from 310 to 340° C.

Propylene loading of the fixed catalyst bed in an inventive heterogeneously catalyzed fixed bed gas phase partial oxidation of propylene to acrolein may thus, for example, be $\geq 80$ l (STP)/l·h or $\geq 90$ l (STP)/l·h and $\leq 300$ l (STP)/l·h, or $\leq 600$ l (STP)/l·h, or $\geq 110$ l (STP)/l·h and $\leq 280$ l (STP)/l·h, or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l (STP)/l·h. In other words, another useful inventive propylene loading of the fixed catalyst bed is the range of $\geq 120$ l (STP)/l·h and $\leq 200$ l (STP)/l·h or $\leq 300$ l (STP)/l·h.

Preferably in accordance with the invention, temperature zone A in the operation of the freshly charged fixed catalyst bed extends up to a conversion $C^A$ of propylene of from 30 or from 40 to 80 mol %, or from 50 to 70 mol %, of from 60 to 70 mol %. Advantageously in accordance with the invention, also during the inventive long-term operation of a heterogeneously catalyzed fixed bed gas phase partial oxidation of propylene to acrolein, the propylene conversions $C^A$ are within one of the aforementioned conversion ranges. They tend to shift to lower molar percentages during the long-term operation.

When the process according to the invention over the freshly charged fixed catalyst bed is a heterogeneously catalyzed fixed bed gas phase partial oxidation of acrolein to acrylic acid, the differences recommended as advantageous $T^{maxA}-T^{maxB}$ (for example $\geq 0°$ C. and $\leq 80°$ C., frequently $\geq 1°$ C. and $\leq 70°$ C., often $\geq 2°$ C. and $\leq 60°$ C., in many cases $\geq 3°$ C. and $\leq 50°$ C., advantageously $\geq 4°$ C. and $\leq 40°$ C., preferably $\geq 5°$ C. and $\leq 30°$ C., or $\leq 20°$ C., more preferably $\geq 5°$ C. and $\leq 15°$ C., or else $\geq 0°$ C. and $\leq 5°$ C.), in the case of relatively low ($\geq 60$ l (STP)/l·h or $\leq 70$ l (STP)/l·h and $\leq 120$ l (STP)/l·h or $\leq 100$ l (STP)/l·h) acrolein loadings on the fresh fixed catalyst bed, are frequently established when firstly both the temperature of temperature zone A and the temperature of temperature zone B are in the range from 230 to 320° C. and secondly the difference between the temperature of temperature zone B ($T^B$) and the temperature of temperature zone A ($T^A$), i.e. $\Delta T^{BA}=T^A-T^B$, is $>0°$ C. and $\leq 20°$ C. or $\leq 10°$ C., or $>0°$ C. and $\leq 5°$ C., or frequently $>0°$ C. and $\leq 3°$ C. (in this case, the temperature of temperature zone B in the inventive long-term operation would necessarily be increased (preferably constantly) and at least one of operating modes a) to c) applied to the temperature of temperature zone A (the whole process preferably in such a way that $T^{maxA}-T^{maxB} \geq 0°$ C. is maintained)). The temperatures of the two temperature zones A, B preferably remain within the temperature range from 230 to 320° C. or to 340° C.

When the heterogeneously catalyzed fixed bed gas phase partial oxidation of acrolein to acrylic acid is practised with increased acrolein loadings on the fresh fixed catalyst bed ($>120$ l (STP)/l·h, (but if appropriate also even at $>100$ l (STP)/l·h), or 130 l (STP)/l·h, or $\geq 140$ l (STP)/l·h, or $\geq 150$ l (STP)/l·h and generally $\leq 175$, or $\leq 200$ or $\leq 300$ l (STP)/l·h, or normally $\leq 600$ l (STP)/l·h), the differences $T^{maxA}-T^{maxB}$ recommended as advantageous (see above) over the fresh fixed catalyst bed are normally established when firstly both the temperature of temperature zone A and the temperature of temperature zone B are in the range from 230 to 320 or to 340° C. and secondly the difference between the temperature of temperature zone B ($T^B$) and the temperature of temperature zone A ($T^A$), i.e. $\Delta T^{BA}=T^B-T^A$, is $\geq 0°$ C. and $\leq 50°$ C., or $\geq 5°$ C. and $\leq 45°$ C., or $\geq 10°$ C. and $\leq 40°$ C., or $\geq 15°$ C. and $\leq 30°$ C., or $\leq 35°$ C. (for example 20° C. or 25° C.), or $\geq 10°$ C. and $\leq 25°$ C., or $\leq 20°$ C., or $\leq 15°$ C. (in this case, the temperature of temperature zone A in the inventive long-term operation would necessarily be increased (preferably constantly) and at least one of operating modes a) to c) applied to the temperature of temperature zone B (the whole process preferably in such a way that $T^{maxA}-T^{maxB} \geq 0°$ C. is maintained; preferably operating mode c))).

The temperatures of the two temperature zones A, B preferably remain in the temperature range from 230 to 320 or to 340° C.

Advantageously, the temperature of temperature zone A in an inventive heterogeneously catalyzed fixed bed gas phase partial oxidation of acrolein to acrylic acid (irrespective of the acrolein loading of the fixed catalyst bed) during the inventive long-term operation (and during the operation of the fresh charge) is within the preferred range of from 250 to 300° C. or in the more preferred range of from 260 to 280° C.

Acrolein loading of the fixed catalyst bed in an inventive heterogeneously catalyzed fixed bed gas phase partial oxidation may thus, for example, be $\geq 60$ l (STP)/l·h or $\geq 70$ l (STP)/l·h or $\geq 90$ l (STP)/l·h, and generally $\leq 300$ l (STP)/l·h or typically $\leq 600$ l (STP)/l·h, or $\geq 110$ l (STP)/l·h and $\leq 280$ l (STP)/l·h, or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l (STP)/l·h.

In other words, the acrolein loading of the fixed catalyst bed may, in accordance with the invention, also be from $\geq 90$ l (STP)/l·h to $\leq 150$ l (STP)/l·h or $\leq 300$ l (STP)/l·h.

Preferably in accordance with the invention, temperature zone A in the operation of the freshly charged fixed catalyst bed extends up to a conversion $C^A$ of acrolein of from 30 or from 40 to 85 mol %, or from 50 to 85 mol %, or from 60 to 85 mol %.

Advantageously in accordance with the invention, also during the inventive long-term operation of a heterogeneously catalyzed fixed bed gas phase partial oxidation of acrolein to acrylic acid, the acrolein conversions $C^A$ are within one of the aforementioned conversion ranges. They tend to shift to lower molar percentages during the long-term operation.

The working pressure both in the inventive heterogeneously catalyzed gas phase partial oxidation of propylene to acrolein and of acrolein to acrylic acid may be below standard pressure (for example from 0.5 to 1 atm) or above standard pressure. Typically, the working pressure in both inventive partial oxidations will be at values of from 1 to 5 atm, frequently from 1 to 3 atm. Normally, the working pressure (reaction pressure) in both partial oxidations will not exceed 100 atm.

In general, the propylene conversion $C^B$ in an inventive heterogeneously catalyzed partial gas phase oxidation of propylene to acrolein (based on single pass of the reaction gas mixture through the fixed catalyst bed) will be $\geq 90$ mol %, or $\geq 92$ mol %, or $\geq 94$ mol %. The selectivity of product of value formation (sum of acrolein formation and acrylic acid by-product formation) will, in the event of suitable selection of the fixed catalyst charge in a manner known per se, regularly be $\geq 80$ mol %, or $\geq 85$ mol %, or $\geq 90$ mol %, or $\geq 92$ mol %, or $\geq 94$ mol %, frequently $\geq 95$ mol %, or $\geq 96$ mol % or $\geq 97$ mol %.

In general, the acrolein conversion $C^B$ in an inventive heterogeneously catalyzed partial gas phase oxidation of acrolein to acrylic acid (based on single pass of the reaction gas mixture through the fixed catalyst bed) will be $\geq 90$ mol %, or $\geq 92$ mol %, or $\geq 94$ mol %, or $\geq 96$ mol %, or $\geq 98$ mol % and frequently even $\geq 99$ mol % and more. The selectivity of acrylic acid formation will, in the event of suitable selection of the fixed bed catalyst charge in a manner known per se, regularly be $\geq 80$ mol %, or $\geq 85$ mol %, or $\geq 90$ mol %, or $\geq 92$ mol %, or $\geq 94$ mol %, frequently $\geq 95$ mol %, or $\geq 96$ mol % or $\geq 97$ mol %.

The molar ratio of $O_2:C_3H_6$ in the reaction gas input mixture for an inventive partial oxidation of propylene to acrolein will, in accordance with the invention, normally be $\geq 1$. Typically, this ratio will be at values of $\leq 3$. Frequently, the molar ratio of $O_2:C_3H_6$ for the aforementioned reaction is, in accordance with the invention, $\geq 1.2$ or $\geq 1.5$ and $\leq 2.0$.

The molar ratio of $O_2$:acrolein in the reaction gas input mixture for an inventive partial oxidation of acrolein to acrylic acid will, in accordance with the invention, normally be $\geq 0.5$. Typically, this ratio will be at values of $\leq 3$. Frequently, the molar ratio of $O_2$:acrolein for the aforementioned reaction is, in accordance with the invention, $\geq 1.5$ and $\leq 2.0$.

Both for an inventive heterogeneously catalyzed partial oxidation of propylene to acrolein and of acrolein to acrylic, it is favorable when the product gas mixture still comprises (for example up to 3% by volume) of unconverted molecular oxygen.

Useful (fresh) catalysts for the fixed catalyst bed (the fixed bed catalyst charge) of an inventive gas phase partial oxidation of propylene to acrolein are all of those whose active composition is at least one multimetal oxide comprising molybdenum and/or tungsten and at least one of the elements bismuth, tellurium, antimony, tin and copper. These include in particular those catalysts whose active composition is at least one multimetal oxide comprising Mo, Bi and Fe.

These are in particular the multimetal oxide active compositions of the general formula I of DE-A 199 55176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700714.

Also suitable for the fresh fixed bed catalyst charge of such a propylene partial oxidation are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This applies in particular to the exemplary embodiments (including the working examples) in these documents, among which particular preference is given to those of Research Disclosure No. 497012, EP-A 15 565, EP-A 575 897, DE-A 197 46 210 and DE-A 198 55 913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}Ox \cdot 10SiO_2$. Emphasis is also given to the example having the serial number 3 from DE-A 198 55 913 (stoichiometry: $Mo_{12}CO_7Fe_3Bi_{0.6}K_{0.08}Si_{1.6}Ox$) as an unsupported hollow cylinder catalyst of geometry 5 mm×3 mm×2 mm or 5 mm×2 mm×2 mm (each external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is true especially when they have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable are the multimetal oxide catalysts and geometries of DE-A 101 01 695 or WO 02/062737.

Also suitable are example 1 of DE-A 10046957 (stoichiometry: $[Bi_2W_2O_9 \cdot 2WO_3]_{0.5}$·

[Mo$_{12}$Co$_{5.6}$Fe$_{2.94}$Si$_{1.59}$K$_{0.08}$O$_x$]$_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: Mo$_{12}$Bi$_{1.0}$Fe$_3$CO$_7$Si$_{1.6}$K$_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multitude of multimetal oxide active compositions suitable for the catalysts of the (fresh) fixed bed catalyst charge of an inventive propylene partial oxidation to acrolein can be encompassed by the general formula I

$$Mo_{12}Bi_aFe_bX^1_cX^2_dX^3_eX^4_fO_n \qquad (I)$$

in which the variables are each defined as follows:
X$^1$=nickel and/or cobalt,
X$^2$=thallium, an alkali metal and/or an alkaline earth metal,
X$^3$=zinc, phosphorus, arsenic, boron, antimony, tin, cerium, lead and/or tungsten,
X$^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, NH$_3$, CO and/or H$_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as NH$_4$OH, (NH$_4$)$_2$CO$_3$, NH$_4$NO$_3$, NH$_4$CHO$_2$, CH$_3$COOH, NH$_4$CH$_3$CO$_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

Typically, the multimetal oxide active compositions of the general formula I are used in the (fresh) fixed bed catalyst charge for an inventive propylene partial oxidation to acrolein not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined may also be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1000 µm, preferably within the range from 50 to 500 µm and more preferably within the range from 150 to 250 µm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention in the first reaction stage is based. The support bodies can have a regular or irregular shape, although preference is given to regularly shaped support bodies having distinct surface roughness, for example spheres or hollow cylinders. It is suitable to use substantially nonporous, surface-roughened spherical supports made of steatite (e.g. steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings suitable as support bodies according to the invention, the wall thickness is also typically from 1 to 4 mm. According to the invention, annular support bodies to be used preferably have a length of from 2 to 6 mm, an external diameter of from 4 to 8 mm and a wall thickness of from 1 to 2 mm. Suitable as support bodies according to the invention are in particular rings of the geometry 7 mm×3 mm×4 mm (external diameter×length×internal diameter). It will be appreciated that the fineness of the catalytically active oxide compositions to be applied to the surface of the support body will be adapted to the desired coating thickness (cf. EP-A 714 700).

For the (fresh) catalysts of an inventive partial oxidation of propylene to acrolein, suitable multimetal oxide active compositions are also compositions of the general formula II

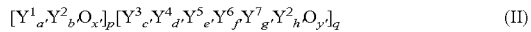 (II)

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in II other than oxygen and
p,q=numbers whose p/q ratio is from 0.1 to 10,
comprising three-dimensional regions of the chemical composition $Y^1_{a'}Y^2_{b'}O_{x'}$ which are delimited from their local environment as a consequence of their different chemical composition from their local environment, and whose maximum diameter (longest line passing through the center of the region and connecting two points on the surface (interface)) is from 1 nm to 100 μm, frequently from 10 nm to 500 nm or from 1 μm to 50 or 25 μm.

Particularly advantageous multimetal oxide compositions II are those in which $Y^1$ is only bismuth.

Among these, preference is given in turn to those of the general formula III

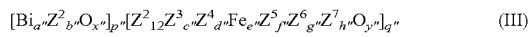 (III)

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the valency and frequency of the elements in III other than oxygen, p",q"=numbers whose p"/q" ratio is from 0.1 to 5, preferably from 0.5 to 2,
and very particular preference is given to those compositions III in which
$Z^2_{b"}$=(tungsten)$_{b"}$ and $Z^2_{12}$=(molybdenum)$_{12}$.

It is also advantageous when at least 25 mol % (preferably at least 50 mol % and more preferably at least 100 mol %) of the total proportion of $[Y^1_aY^2_{b'}O_{x'}]_p([Bi_{a"}Z^2_{b"}O_{x"}]_{p"})$ of the multimetal oxide compositions II (multimetal oxide compositions III) suitable in accordance with the invention in the multimetal oxide compositions II (multimetal oxide compositions III) suitable in accordance with the invention are in the form of three-dimensional regions of the chemical composition $Y^1_{a'}Y^2_{b'}O_{x'}[Bi_{a"}Z^2_{b"}O_{x"}]$ which are delimited from their local environment as a consequence of their different chemical composition from their local environment, and whose maximum diameter is in the range from 1 nm to 100 μm.

With regard to the shaping, the statements made for the multimetal oxide composition I catalysts apply to the multimetal oxide composition II catalysts.

The preparation of multimetal oxide composition II active compositions is described, for example, in EP-A 575 897 and also in DE-A 198 55 913.

The inert support materials recommended above are also useful, inter alia, as inert materials for diluting and/or delimiting the corresponding fixed catalyst bed, or as a protective preliminary bed therefor.

For the (fresh) catalysts of an inventive partial oxidation of acrolein to acrylic acid, useful active compositions are in principle all multimetal oxide active compositions comprising Mo and V, for example those of DE-A 100 46 928.

A multitude thereof, for example those of DE-A 198 15 281, can be encompassed by the general formula IV

 (IV)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in IV other than oxygen.

Embodiments preferred in accordance with the invention among the active multimetal oxides IV are those which are encompassed by the following definitions of the variables of the general formula IV:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and n=a number which is determined by the valency and frequency of the elements in IV other than oxygen.

However, multimetal oxides IV which are very particularly preferred in accordance with the invention are those of the general formula V $$Mo_{12}V_{a'}Y^1_{b'}Y^2_{c'}Y^5_{f'}Y^6_{g'}O_{n'} \quad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in V other than oxygen.

The multimetal oxide active compositions (IV) suitable in accordance with the invention are obtainable in a manner known per se, for example disclosed in DE-A 4335973 or in EP-A 714700.

In principle, multimetal oxide active compositions suitable for the catalysts of the fresh fixed bed catalyst charge of an inventive acrolein partial oxidation to acrylic acid, especially those of the general formula IV, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to intimate mixing in wet form. This is typically done by mixing the starting compounds in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide active compositions, especially those of the general formula IV, are generally not used in the (fresh) fixed bed catalyst charge for the inventive partial oxidation of acrolein to acrylic acid in powder form but rather shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 29 09 671, EP-A 293 859 or by EP-A 714 700.

To coat the support bodies, the powder composition to be applied is appropriately moistened and is dried again after application, for example by means of hot air. The coating thickness of the powder composition applied to the support body is advantageously selected within the range from 10 to 1000 μm, preferably within the range from 50 to 500 μm and more preferably in the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with a grit layer. It is suitable to use substantially nonporous, surface-roughened, spherical supports made of steatite (for example steatite C220 from CeramTec), whose diameter is from 1 to 8 mm, preferably from 4 to 5 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length× internal diameter). It will be appreciated that the fineness of the catalytically active oxide compositions to be applied to the surface of the support body is adapted to the desired coating thickness (cf. EP-A 714 700).

Favorable multimetal oxide active compositions to be used for the catalysts of a (fresh) fixed bed catalyst charge for the inventive acrolein partial oxidation to acrylic acid are also compositions of the general formula VI $$[D]_p[E]_q \quad (VI)$$

in which the variables are each defined as follows:
$D=Mo_{12}V_{a''}Z^1_{b''}Z^2_{c''}Z^3_{d''}Z^4_{e''}Z^5_{f''}Z^6_{g''}O_{x''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a''=from 1 to 8,
b''=from 0.2 to 5,
c''=from 0 to 23, d"=from 0 to 50,
e"=from 0 to 2,
f"=from 0 to 5,
g"=from 0 to 50,
h"=from 4 to 30,
i"=from 0 to 20 and
x",y"=numbers which are determined by the valency and frequency of the elements in VI other than oxygen and
p,q=numbers other than zero whose p/q ratio is from 160:1 to 1:1,
and which are obtainable by separately preforming a multimetal oxide composition E

$$Z^7{}_{12}Cu_{h''}H_{i''}O_{y''} \qquad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D

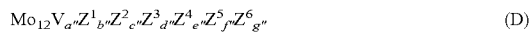
$$Mo_{12}V_{a''}Z^1{}_{b''}Z^2{}_{c''}Z^3{}_{d''}Z^4{}_{e''}Z^5{}_{f''}Z^6{}_{g''} \qquad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to those multimetal oxide compositions VI in which the preformed solid starting composition 1 is incorporated into an aqueous starting composition 2 at a temperature of <70° C. A detailed description of the preparation of multimetal oxide composition VI catalysts is present, for example, in EP-A 668 104, DE-A 197 36 105, DE-A 100 46 928, DE-A 197 40 493 and DE-A 195 28 646.

With regard to the shaping, the statements made for the multimetal oxide composition IV catalysts apply to the multimetal oxide composition VI catalysts.

Additionally suitable as multimetal oxide compositions for the (fresh) catalysts of a fixed catalyst bed for the inventive partial oxidation of acrolein to acrylic acid are those of DE-A 198 15 281, especially all exemplary embodiments from this document. With regard to the shaping, the same applies as was stated above.

Catalysts particularly suitable for the (fresh) fixed bed catalyst charge of a process according to the invention for the partial oxidation of acrolein to acrylic acid are the coated catalysts S1 (stoichiometry: $Mo_{12}V_3W_{1.2}Cu_{2.4}O_n$) and S7 (stoichiometry: $Mo_{12}V_3W_{1.2}Cu_{1.6}Ni_{0.8}O_n$) from DE-A 4442346 with an active composition content of 27% by weight and a coating thickness of 230 μm, the coated catalyst from Preparation Example 5 of DE-A 100 46 928 (stoichiometry: $Mo_{12}V_3W_{1.2}Cu_{2.4}O_n$) with an active composition content of 20% by weight, the coated catalysts according to examples 1 to 5 from DE-A 198 15 281, except, just like the aforementioned coated catalysts for the second reaction stage, applied to support rings of geometry 7 mm×3 mm×4 mm (external diameter×length×internal diameter) with an active composition content of 20% by weight (based on the total mass of the coated catalyst), and also a coated catalyst with biphasic active composition of stoichiometry $(Mo_{10.4}V_3W_{1.2}O_x)(CuMo_{0.5}W_{0.5}W_{0.4})_{1.6}$, and prepared according to DE-A 19736105 and an active composition content of 20% by weight applied to the aforementioned 7 mm×3 mm×4 mm supports.

However, the (fresh) catalysts recommended above for an inventive acrolein partial oxidation to acrylic acid are also suitable for this reaction when everything is retained and only the support geometry is altered to 5 mm×3 mm×1.5 mm (external diameter×length×internal diameter). In addition, the multimetal oxides mentioned may also be used as catalysts for such a partial oxidation in the form of the corresponding unsupported catalyst rings.

In principle, the volume-specific activity of the (fresh) fixed catalyst bed in flow direction of the reaction gas mixture in an inventive partial oxidation of propylene to acrolein may be constant over the length of the flow path (i.e. over the length of the fixed catalyst bed), or advantageously increase at least once (continuously or abruptly or in stages). It is advantageous when the active composition does not change over the length of the flow path of the reaction gas mixture (i.e. within the fresh fixed catalyst bed). The (fresh) fixed catalyst bed for an inventive heterogeneously catalyzed gas phase partial oxidation of propylene to acrolein will be referred to below as fixed catalyst bed 1 or as fixed bed catalyst charge 1. In a corresponding manner, the accompanying reaction gas mixture will be referred to as reaction gas mixture 1 or as reaction gas input mixture 1.

It is advantageous in accordance with the invention when fixed bed catalyst charge 1 consists of at least two spatially successive fixed bed catalyst charge zones, the volume-specific activity within one fixed bed catalyst charge zone being substantially constant and increasing sharply at the transition from one fixed bed catalyst charge zone into another fixed bed catalyst charge zone in flow direction of reaction gas mixture 1.

The volume-specific (i.e. normalized to the unit of the particular bed volume) activity of a fixed bed catalyst charge zone can then be adjusted over the fixed bed catalyst charge zone in a substantially constant manner by starting from a basic amount of shaped catalyst bodies prepared in a uniform manner (their bed corresponds to the maximum achievable volume-specific activity) and homogeneously diluting it in the particular fixed bed catalyst charge zone with shaped bodies (shaped diluent bodies) which behave substantially inertly with regard to the heterogeneously catalyzed partial gas phase oxidation. The higher the proportion of shaped diluent bodies selected, the smaller the amount of active composition and catalyst activity present in a certain volume of the bed. Useful materials for such inert shaped diluent bodies are in principle all of those which are suitable as support material for coated catalysts suitable in accordance with the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned (e.g. steatite C 220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

It is favorable in accordance with the invention, as already stated, when the chemical composition of the active composition used does not vary over the entire fixed bed catalyst charge 1. In other words, although the active composition used for a single shaped catalyst body can be a mixture of different multimetal oxides comprising the elements Mo, Fe and Bi, the same mixture then has to be used for all shaped catalyst bodies of fixed bed catalyst charge 1.

A volume-specific activity increasing zone by zone (is particularly advantageous) over the fixed bed catalyst charge in flow direction of reaction gas mixture 1 can therefore be achieved in a simple manner, for example, by beginning the bed in a first fixed bed catalyst charge zone with a high proportion of inert shaped diluent bodies based on one type of shaped catalyst bodies, and then reducing this proportion of shaped diluent bodies zone by zone in flow direction.

However, such a zone by zone increase in the volume-specific activity advantageous in accordance with the invention is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher active composition content zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bulk density (for example, in the case of unsupported catalysts having identical active composition of the different geometries). It is of course also possible to use the variants described in combination.

It is of course also possible to use mixtures of catalysts having chemically different active compositions and, as a consequence of this different composition, having different activity for fixed bed catalyst charge 1. These mixtures may in turn, zone by zone, be varied in their composition and/or be diluted with different amounts of inert shaped diluent bodies so that the volume-specific activity in flow direction of the reaction gas mixture increases zone by zone.

Upstream and/or downstream of fixed bed catalyst charge 1 may be disposed beds consisting exclusively of inert material (for example only shaped diluent bodies) (in this document, they are not included for terminology purposes in fixed bed catalyst charge 1, since they do not comprise any shaped bodies which have multimetal oxide active composition). The shaped diluent bodies used for the inert bed may have the same geometry as the shaped catalyst bodies used in fixed bed catalyst charge 1. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm or 7 mm×3 mm×4 mm (in each case external diameter×length×internal diameter) or the spherical geometry having a diameter d=4-5 mm. Temperature zones A and B in the process according to the invention may also extend to the inert beds. According to the invention, it is advantageous when neither temperature zone A nor temperature zone B covers more than three fixed bed catalyst charge zones (according to the invention, at least one fixed bed catalyst charge zone is advantageously covered by both temperature zones).

According to the invention, it is particularly preferred when the entire fixed bed catalyst charge comprises not more than five, appropriately not more than four or three, fixed bed catalyst charge zones.

According to the invention, at the transition from one fixed bed catalyst charge zone to another fixed bed catalyst charge zone (in flow direction of reaction gas mixture 1) of fixed bed catalyst charge 1, the volume-specific active composition (i.e. the weight of the multimetal oxide active composition present in a uniform bed volume) should (in the case of uniform active composition over the entire fixed bed catalyst charge 1) appropriately increase by at least 5% by weight, preferably by at least 10% by weight (this applies in particular in the case of uniform shaped catalyst bodies over the entire fixed bed catalyst charge 1). In general, this increase in the process according to the invention for heterogeneously catalyzed partial oxidation of propylene to acrolein will not be more than 50% by weight, usually not more than 40% by weight. According to the invention, in the case of uniform active composition over the entire fixed bed catalyst charge 1, the difference in the volume-specific active composition of the fixed bed catalyst charge zone having the lowest volume-specific activity and the fixed bed catalyst charge zone having the highest volume-specific activity should advantageously also not be more than 50% by weight, preferably not more than 40% by weight, and generally not more than 30% by weight.

In a process according to the invention for heterogeneously catalyzed partial oxidation of propylene to acrolein, the fixed bed catalyst charge 1 will frequently consist of only two fixed bed catalyst charge zones.

According to the invention, preference is given to the last fixed bed catalyst charge zone of fixed bed catalyst charge 1 in flow direction of reaction gas mixture 1 being undiluted. In other words, it preferably consists exclusively of shaped catalyst bodies. If required, it may also consist of a bed of shaped catalyst bodies whose volume-specific activity is reduced, for example by dilution with inert material, for example by 10%.

When fixed bed catalyst charge 1 for a heterogeneously catalyzed partial oxidation of propylene to acrolein consists of only two fixed bed catalyst charge zones, it is generally advantageous in accordance with the invention when the fixed bed catalyst charge zone having the highest volume-specific activity does not project into temperature zone A (especially when the heating in temperature zone A and temperature zone B is effected by means of a flowing heat carrier which in each case flows in countercurrent to the reaction gas mixture viewed over the reactor). In other words, the fixed bed catalyst charge zone having the lower volume-specific activity will favorably project into temperature zone B and the fixed bed catalyst charge zone having the higher volume-specific activity will begin and end in temperature zone B (i.e. have its beginning beyond the transition from temperature zone A to temperature zone B).

Especially at loadings of fixed bed catalyst charge 1 with propylene in the range from 100 to 160 l (STP)/l·h and/or with additional use of, based on reaction gas input mixture 1, for example, up to 50% by volume of propane as an inert diluent gas, it has, however, been found to be appropriate to allow the fixed bed catalyst charge with the highest volume-specific activity to project into temperature zone A. This is especially true in the case of countercurrent mode (viewed over the reactor) of salt baths and reaction gas mixture.

When fixed bed catalyst charge 1 consists only of three fixed bed catalyst charge zones, it is generally equally advantageous in accordance with invention when the fixed bed catalyst charge zone having the higher volume-specific activity does not project into temperature zone A but begins and ends in temperature zone B, i.e. has its beginning beyond the transition from temperature zone A to temperature zone B (especially when the heating in temperature zone A and in temperature zone B is effected by means of a flowing heat carrier which in each case flows in countercurrent to the reaction gas mixture). In other words, the fixed bed catalyst charge zone having the second highest volume-specific activity in this case will normally project into both temperature zone A and temperature zone B.

When fixed bed catalyst charge 1 consists of four fixed bed catalyst charge zones, it is generally advantageous in accordance with the invention when the fixed bed catalyst charge zone having the third highest volume-specific activity projects into both temperature zone A and into temperature zone B (especially when the heating in temperature zone A and in temperature zone B is effected by means of a flowing heat carrier which in each case flows in countercurrent to reaction gas mixture 1).

In the case of cocurrent flow of reaction gas mixture 1 and heat carriers in temperature zones A and B, it may be advantageous in the process according to the invention when the fixed bed catalyst charge zone having the highest volume-specific activity within fixed bed catalyst charge 1 projects into temperature zone A.

Generally, the volume-specific activity between two fixed bed catalyst charge zones of a fixed bed catalyst charge 1 can be differentiated experimentally in a simple manner by passing the same reaction gas mixture comprising propene, under identical boundary conditions (preferably the conditions of the contemplated process), over fixed bed catalyst charges of the same length, but in each case each according to the composition of the particular fixed bed catalyst charge zone. The higher amount of propene converted indicates the higher volume-specific activity.

When the total length of fixed bed catalyst charge 1 is $L^1$, it is advantageous in accordance with the invention if there is no transition from one fixed bed catalyst charge zone to another fixed bed catalyst charge zone within the region of $$X^1 \pm L^1 \frac{4}{100}$$

or within the region of $$X^1 \pm L^1 \frac{3}{100}$$

or within the region of $$X^1 \pm L^1 \frac{2}{100},$$

where X is the location (the position) within fixed bed catalyst charge 1 of the transition from temperature zone A to temperature zone B.

Preference in accordance with the invention is given to fixed bed catalyst charge 1 in the process according to the invention being structured as follows in flow direction of reaction gas mixture 1.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed bed catalyst charge 1, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. According to the invention, this first zone of the fixed bed catalyst charge 1 is advantageously followed up to the end of the length of the fixed bed catalyst charge 1 (i.e., for example, to a length of from 1.00 (or 1.40 m) to 3.00 m, preferably from 2.00 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies especially when the shaped catalyst bodies used in the fixed bed catalyst charge 1 are unsupported catalyst rings or coated catalyst rings (in particular those which are specified as preferred in this document). For the purposes of the abovementioned structuring, both the shaped catalyst bodies and the shaped diluent bodies in the process according to the invention advantageously have substantially the ring geometry 5 mm×3 mm×2 mm (external diameter×length× internal diameter).

The aforementioned also applies when, instead of inert shaped diluent bodies, shaped coated catalyst bodies are used whose active composition content is from 2 to 15% by weight lower than the active composition content of any shaped coated catalyst bodies used at the end of fixed bed catalyst charge 1.

A pure inert material bed whose length, based on the length of fixed bed catalyst charge 1, is appropriately from 5 to 20% generally precedes fixed bed catalyst charge 1 in flow direction of the reaction gas mixture. It is normally utilized as a heating zone for reaction gas mixture 1.

According to the invention, the fixed bed catalyst charge zone having the lower volume-specific activity in the aforementioned fixed bed catalyst charges 1 then advantageously extends into temperature zone B for from 5 to 20%, frequently from 5 to 15%, of its length.

Appropriately in accordance with the invention, temperature zone A also extends to a preliminary bed of inert material which is used if appropriate for fixed bed catalyst charge 1.

In principle, the volume-specific activity of the (fresh) fixed catalyst bed in flow direction of the reaction gas mixture in an inventive partial oxidation of acrolein to acrylic acid may be constant over the length of the flow path (i.e. over the length of the fixed catalyst bed), or advantageously increase at least once (continuously or abruptly or in stages). It is advantageous when the active composition does not change over the length of the flow path of the reaction gas mixture (i.e. within the fresh fixed catalyst bed). The (fresh) fixed catalyst bed for an inventive heterogeneously catalyzed gas phase partial oxidation of acrolein to acrylic acid will be referred to below as fixed catalyst bed 2 or as fixed bed catalyst charge 2. In a corresponding manner, the accompanying reaction gas mixture is referred to as reaction gas mixture 2 or as reaction gas input mixture 2.

It is advantageous in accordance with the invention when fixed bed catalyst charge 2 consists of at least two spatially successive fixed bed catalyst charge zones, the volume-specific activity within one fixed bed catalyst charge zone being substantially constant and increasing sharply at the transition from one fixed bed catalyst charge zone into another fixed bed catalyst charge zone in flow direction of reaction gas mixture 2.

The volume-specific (i.e. normalized to the unit of the particular bed volume) activity of a fixed bed catalyst charge zone can then be adjusted over the fixed bed catalyst charge zone in a substantially constant manner by starting from a basic amount of shaped catalyst bodies prepared in a uniform manner (their bed corresponds to the maximum achievable volume-specific activity) and homogeneously diluting it in the particular fixed bed catalyst charge zone with shaped bodies (shaped diluent bodies) which behave substantially inertly with regard to the heterogeneously catalyzed partial gas phase oxidation. The higher the proportion of shaped diluent bodies selected, the less the amount of active composition and catalyst activity present in a certain volume of the bed. Useful materials for such inert shaped diluent bodies are in principle all of those which are suitable as support material for coated catalysts suitable in accordance with the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned (e.g. steatite C 220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

It is favorable in accordance with the invention, as already stated, when the chemical composition of the active composition used does not vary over the entire fixed bed catalyst charge 2. In other words, although the active composition used for a single shaped catalyst body can be a mixture of different multimetal oxides, for example comprising the elements Mo and V, the same mixture then has to be used for all shaped catalyst bodies of fixed bed catalyst charge 2.

A volume-specific activity increasing zone by zone (is particularly advantageous) over the fixed bed catalyst charge 2 in flow direction of reaction gas mixture 2 can therefore be achieved for the process according to the invention in a simple manner, for example, by beginning the bed in a first fixed bed catalyst charge zone with a high proportion of inert shaped diluent bodies based on one type of shaped catalyst bodies, and then reducing this proportion of shaped diluent bodies zone by zone in flow direction.

However, such a zone by zone increase in the volume-specific activity advantageous in accordance with the invention is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher active composition content zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bulk density (for example, in the case of unsupported catalysts having identical active composition of the different geometries). It is of course also possible to use the variants described in combination.

It is of course also possible to use mixtures of catalysts having chemically different active compositions and, as a consequence of this different composition, having different activity for fixed bed catalyst charge 2. These mixtures may in turn, zone by zone, be varied in their composition and/or be diluted with different amounts of inert shaped diluent bodies.

Upstream and/or downstream of fixed bed catalyst charge 2 may be disposed beds consisting exclusively of inert material (for example only shaped diluent bodies) (in this layer, they are not included for terminology purposes in fixed bed catalyst charge 2, since they do not comprise any shaped bodies which have multimetal oxide active composition). The shaped diluent bodies used for the inert bed may have the same geometry as the shaped diluent bodies used in fixed bed catalyst charge 2. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm or 7 mm×3 mm×4 mm (in each case external diameter×length×internal diameter) or the spherical geometry having the diameter d=4-5 mm. Temperature zones A and B in the process according to the invention may also extend to the inert beds. According to the invention, it is advantageous when neither temperature zone A nor temperature zone B covers more than three fixed bed catalyst charge zones (according to the invention, at least one fixed bed catalyst charge zone is advantageously covered by both temperature zones).

According to the invention, it is particularly preferred when the entire fixed bed catalyst charge 2 comprises not more than five, appropriately not more than four or three, fixed bed catalyst charge zones.

According to the invention, at the transition from one fixed bed catalyst charge zone to another fixed bed catalyst charge zone (in flow direction of reaction gas mixture 2) the volume-specific active composition (i.e. the weight of the multimetal oxide active composition present in a uniform bed volume) should (in the case of uniform active composition over the entire fixed bed catalyst charge 2) appropriately increase by at least 5% by weight, preferably by at least 10% by weight (this applies in particular in the case of uniform shaped catalyst bodies over the entire fixed bed catalyst charge 2). In general, this increase in a process according to the invention for heterogeneously catalyzed partial oxidation of acrolein to acrylic acid will not be more than 50% by weight, usually not more than 40% by weight. According to the invention, in the case of uniform active composition over the entire fixed bed catalyst charge 2, the difference in the volume-specific active composition of the fixed bed catalyst charge zone having the lowest volume-specific activity and the fixed bed catalyst charge zone having the highest volume-specific activity should advantageously also not be more than 50% by weight, preferably not more than 40% by weight, and more preferably not more than 30% by weight.

In a process according to the invention for heterogeneously catalyzed partial oxidation of acrolein to acrylic acid, fixed bed catalyst charge 2 will frequently consist of only two fixed bed catalyst charge zones.

Preferably in accordance with the invention, the last fixed bed catalyst charge zone of fixed bed catalyst charge 2 in flow direction of reaction gas mixture 2 is undiluted. In other words, it preferably consists exclusively of shaped catalyst bodies. If required, it may also consist of a bed of shaped catalyst bodies whose volume-specific activity is reduced, for example by dilution with inert material, for example by 10%.

When fixed bed catalyst charge 2 for a heterogeneously catalyzed partial oxidation of acrolein to acrylic acid consists of only two fixed bed catalyst charge zones, it is generally advantageous in accordance with the invention when the fixed bed catalyst charge zone having the highest volume-specific activity projects into temperature zone A (especially when the heating in temperature zone A and temperature zone B is effected by means of a flowing heat carrier which in each case flows in countercurrent (viewed over the reactor) to the reaction gas mixture 2).

When fixed bed catalyst charge 2 consists only of three fixed bed catalyst charge zones, it is generally equally advantageous in accordance with the invention when the fixed bed catalyst charge zone having the highest volume-specific activity projects into temperature zone A (especially when the heating in temperature zone A and in temperature zone B is effected by means of a flowing heat carrier which in each case flows in countercurrent to the reaction gas mixture 2).

When fixed bed catalyst charge 2 consists of four fixed bed catalyst charge zones, it is generally advantageous in accordance with the invention when the fixed bed catalyst charge zone having the second highest volume-specific activity projects into both temperature zone A and into temperature zone B (especially when the heating in temperature zone A and in temperature zone B is effected by means of a flowing heat carrier which in each case flows in countercurrent to reaction gas mixture 2).

In the case of cocurrent flow of reaction gas mixture 2 and heat carriers in temperature zones A and B, it may be advantageous in accordance with the invention when the fixed bed catalyst charge zone having the highest volume-specific activity within fixed bed catalyst charge 2 does not project into temperature zone A but rather only has its beginning beyond the transition from temperature zone A to temperature zone B.

The volume-specific activity between two fixed bed catalyst charge zones of the fixed bed catalyst charge 2 can be differentiated experimentally in a simple manner by passing the same reaction gas mixture comprising acrolein, under identical boundary conditions (preferably the conditions of the contemplated process), over fixed bed catalyst charges of the same length, but in each case each according to the composition of the particular fixed bed catalyst charge zone. The higher amount of acrolein converted indicates the higher volume-specific activity.

When the total length of fixed bed catalyst charge 2 is $L^2$, it is advantageous in accordance with the invention if there is no transition from one fixed bed catalyst charge zone to another fixed bed catalyst charge zone within the region of $$X^2 \pm L^2 \frac{4}{100}$$

or within the region of $$X^2 \pm L^2 \frac{3}{100}$$

or within the region of $$X^2 \pm L^2 \frac{2}{100},$$

where X is the location within fixed bed catalyst charge 2 of the transition from temperature zone A to temperature zone B.

Preferably in accordance with the invention, fixed bed catalyst charge 2 in the process according to the invention is structured as follows in flow direction of reaction gas mixture 2.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed bed catalyst charge 2, a homogeneous mixture or two (having decreasing dilution) successive homogeneous mixtures of shaped catalyst bodies and shaped diluent bodies (both preferably having substantially the same geometry), in which the proportion of shaped diluent bodies is such that the volume-specific active composition, based on a bed consisting only of shaped catalyst bodies, has been reduced by from 10 to 50% by weight, preferably from 20 to 45% by weight and more preferably from 25 to 35% by weight. According to the invention, this first zone or these first two zones of fixed bed catalyst charge 2 are then advantageously followed to the end of the length of fixed bed catalyst charge 2 (i.e., for example, to a length of from 1.00 (or 1.50) to 3.50 m, preferably from 2.00 to 3.00 m) by either a bed of the shaped catalyst bodies diluted only to a slighter extent (than in the first zone or in the first two zones) or, most preferably, an unaccompanied bed of the same shaped catalyst bodies which have also been used in the first zones.

The aforementioned applies in particular when the shaped catalyst bodies used in fixed bed catalyst charge 2 are coated catalyst rings or coated catalyst spheres (in particular those which are listed in this document as preferred). It is advantageous when, for the purposes of the aforementioned structuring, both the shaped catalyst bodies or their support rings and the shaped diluent bodies in the process according to the invention substantially have the ring geometry 7 mm×3 mm×4 mm (external diameter×length×internal diameter).

The abovementioned also applies when, instead of inert shaped diluent bodies, shaped coated catalyst bodies are used whose active composition content is from 2 to 15% by weight lower than the active composition content of the shaped coated catalyst bodies at the end of the fixed bed catalyst charge 2.

A pure inert material bed whose length, based on the length of fixed bed catalyst charge 2, is appropriately from 5 to 20% generally commences fixed bed catalyst charge 2 in flow direction of the reaction gas mixture. It normally serves the purpose of heating reaction gas mixture 2.

It is advantageous in accordance with the invention when temperature zone A (which also advantageously extends in accordance with the invention to the preliminary bed of inert material) in the aforementioned fixed bed catalyst charges 2 extends for from 5 to 20%, frequently from 5 to 15%, of the length of the last (volume-specifically most active) fixed bed catalyst charge zone of fixed bed catalyst charge 2 in flow direction of reaction gas mixture 2.

It will be appreciated that temperature zones A, B in the process according to the invention may be followed by further additional temperature zones. However, this is not preferred in accordance with the invention.

For coated catalysts (for example of fixed bed catalyst charges 1 or 2), especially suitable support bodies are those which have an increased surface roughness, since they generally cause increased adhesive strength of the coating of active composition applied.

The surface roughness $R_Z$ of the support body is preferably in the range from 30 to 200 μm, preferably from 30 to 100 μm (determined to DIN 4768 sheet 1 with a Hommel tester for DIN-ISO surface measurements from Hommelwerke). The aforementioned is especially true for support bodies of steatite C 220 from CeramTec. In principle, the support materials may be porous or nonporous.

In an appropriate manner from an application point of view, a process according to the invention for partial oxidation of propylene to acrolein is carried out in a two-zone tube bundle reactor, as described, for example, in DE-As 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out such a process.

In other words, in the simplest manner, the fixed bed catalyst charge 1 to be used in accordance with the invention for such a process (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (temperature zone A) in which the oxidative conversion of propene (in single pass) proceeds until a conversion $C^A$ in the range required in accordance with the invention is achieved, and a salt bath B flows around the section of the tubes (temperature zone B) in which the subsequent oxidative conversion of propene (in single pass) proceeds until a conversion value $C^B$ of at least 90 mol % is achieved (if required, the temperature zones A, B to be used in accordance with the invention may be followed by further temperature zones which are maintained at individual temperatures).

It is appropriate from an application point of view for an inventive propylene partial oxidation to acrolein not to include any further temperature zones. In other words, salt bath B appropriately flows around the section of the tubes in which the subsequent oxidative conversion of propene (in single pass) proceeds up a conversion value of $\geqq 90$ mol %, or $\geqq 92$ mol % or $\geqq 94$ mol % or more.

According to the invention, both salt baths A, B can be conducted in cocurrent or in countercurrent through the space surrounding the reaction tubes relative to flow direction of reaction gas mixture 1 flowing through the reaction tubes. It is of course also possible in accordance with the invention to employ cocurrent flow in temperature zone A and countercurrent flow in temperature zone B (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700 714 or in EP-A 700 893, which results overall in a meandering flow profile of the heat exchange medium in a longitudinal section through the catalyst tube bundle.

Appropriately, a reaction gas input mixture 1 is fed to fixed bed catalyst charge 1 preheated to the temperature of the temperature zone A.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is appropriately from 2 to 4 m, preferably from 2.5 to 3.5 m. In each temperature zone, the fixed bed catalyst charge 1 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or to 40 000. Tube bundle reactors having a number of catalyst tubes above 50 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf., for example, EP-B 468 290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the temperature zone to the exit from the temperature zone (as a result of the exothermicity of the reaction) by from 0 to 15° C. In other words, the aforementioned $\Delta T$ may, in accordance with the invention, be from 1 to 10° C., or from 2 to 8° C., or from 3 to 6° C.

The entrance temperatures of the heat exchange media into temperature zones A, B of the two-zone tube bundle reactors in a propylene partial oxidation to acrolein are to be selected in accordance with the invention such that they correspond to the temperatures and temperature differences $\Delta T^{B,A}$ required for temperature zones A, B in this document for this reaction. In inventive long-term operation, they are to be changed in accordance with the invention.

It should be pointed out once again here that, for the performance of an inventive propylene partial oxidation to acrolein, it is also possible in particular to use the two-zone tube bundle reactor type which is described in DE-B 2201528 and includes the possibility of removing a portion of the hot heat exchange medium of temperature zone B to temperature zone A, in order if appropriate to heat a cold reaction gas input mixture 1 or a cold cycle gas. The tube bundle characteristics within an individual temperature zone may also be configured as described in EP-A 382098.

In the case of a two-stage heterogeneously catalyzed partial oxidation of propylene to acrylic acid, appropriately in accordance with the invention, two two-zone processes according to the invention will be connected in series. An inventive partial oxidation of propylene to acrolein forms the first reaction stage and an inventive partial oxidation of acrolein to acrylic acid forms the second stage connected downstream of the first stage.

In this case, it is appropriate to cool the product gas mixture leaving the first reaction stage in a direct and/or indirect manner before it enters the second reaction stage, in order thus to suppress subsequent complete combustion of portions of the acrolein formed in the first reaction stage. To this end, an aftercooler is typically connected between the two reaction stages. In the simplest case, this may be an indirect tube bundle heat transferrer. In this case, the product gas mixture is generally conducted through the tubes and a heat exchange medium is conducted around the tubes and may be of the type corresponding to the heat exchange media recommended for the tube bundle reactors. Advantageously, the tube interior is filled with inert random packings (for example spirals of stainless steel, rings of steatite, spheres of steatite, etc.). These improve the heat exchange and capture any molybdenum trioxide subliming from the fixed bed catalyst charge of the first reaction stage before it enters the second reaction stage. It is advantageous for the aftercooler to be manufactured from stainless steel coated with zinc silicate primer.

Useful sources for the molecular oxygen required in the first reaction stage include both air and air depleted of molecular nitrogen (for example, $\geq 90\%$ by volume of $O_2$, $\leq 10\%$ by volume of $N_2$).

It is appropriate from an application point of view to cool the product gas mixture of the first reaction stage in the aftercooler already mentioned to a temperature of from 210 to 290° C., frequently from 230 to 280° C. or from 250 to 270° C. The product gas mixture of the first reaction stage can quite possibly be cooled to temperatures which are below the temperature of temperature zone A. However, the aftercooling described is in no way obligatory and can generally be dispensed with, especially when the path of the product gas mixture from the first reaction stage to the second reaction stage is kept short. Typically, such a two-stage process according to the invention is also implemented in such a way that the oxygen requirement in the second reaction stage is not already covered by an appropriately high oxygen content of reaction gas input mixture 1, but rather that the required oxygen is added in the region between the first and second reaction stages ("secondary gas addition"). This may be effected before, during, after and/or for aftercooling. Useful sources for the molecular oxygen required in the second reaction stage include both pure oxygen and mixtures of oxygen and inert gas, for example air or air depleted of molecular nitrogen (for example, $\geq 90\%$ by volume of $O_2$, $\leq 10\%$ by volume of $N_2$). The oxygen source is regularly added compressed to the reaction pressure. In such a two-stage process, the oxygen requirement in the second reaction stage can of course already be covered by an appropriately high oxygen requirement in the first reaction stage. If required, an inert diluent gas can of course also be added as a secondary gas.

Like the performance of the first reaction stage, the second reaction stage of such a two-stage process is also performed in an appropriate manner from an application point of view in a two-zone tube bundle reactor, as has already been described for the first reaction stage. The remarks regarding the two-zone tube bundle reactor for the first reaction stage therefore also apply to the two-zone tube bundle reactor for the second reaction stage (this is also true when a "second reaction stage" is carried out independently of a preceding first reaction stage).

In other words, in a simple manner, the fixed bed catalyst charge 2 (if appropriate including the inert beds) to be used for a second reaction stage or generally for an inventive heterogeneously catalyzed partial oxidation of acrolein to acrylic acid is also disposed in the metal tubes of a tube bundle reactor and two substantially spatially separated heating media, generally salt melts, are conducted around the metal tubes. According to the invention, the tube section over which the respective salt bath extends represents a temperature zone.

In other words, in a simple manner, for example, a salt bath A flows around those sections of the tubes (temperature zone A) in which the oxidative conversion of acrolein (in single pass) proceeds until a $C^A$ in the range required in accordance with the invention is achieved, and a salt bath B flows around the section of the tubes (temperature zone B) in which the subsequent oxidative conversion of acrolein (in single pass) proceeds until a conversion value of at least 90 mol % is achieved (if required, the temperature zones A, B to be used in accordance with the invention may be followed by further temperature zones which are maintained at individual temperatures).

It is appropriate from an application point of view for an inventive acrolein partial oxidation also not to include any further temperature zones. In other words, salt bath B appropriately flows around the section of the tubes in which the subsequent oxidative conversion of acrolein (in single pass) proceeds up to a conversion value of $\geq 92$ mol %, or $\geq 94$ mol % or $\geq 96$ mol % or $\geq 98$ mol % and frequently even $\geq 99$ mol % or more.

According to the invention, both salt baths A, B can be conducted in cocurrent or in countercurrent through the space surrounding the reaction tubes relative to the flow direction of reaction gas mixture 2 flowing through the reaction tubes. It is of course also possible in accordance with the invention to employ cocurrent flow in temperature zone A and countercurrent flow in temperature zone B (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700 714 or in EP-A 700 893, which results overall in a meandering flow profile of the heat exchange medium in a longitudinal section through the catalyst tube bundle.

Appropriately, a reaction gas input mixture 2 is fed to fixed bed catalyst charge 2 preheated to the temperature of zone A.

Typically, the catalyst tubes in the aforementioned two-zone tube bundle reactors for the second reaction stage are manufactured from ferritic steel and typically have a wall thickness of from 1 to 3 mm. Their internal diameter is generally from 20 to 30 mm, frequently from 21 to 26 mm. Their length is appropriately from 3 to 4 m, preferably 3.5 m. In each temperature zone, fixed bed catalyst charge 2 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000 or to 40 000. Tube bundle reactors having a number of catalyst tubes above 50 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf. EP-B 468 290).

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-zone tube bundle reactors of the second reaction stage, the flow rate within the two heat exchange medium circuits required is selected in such a way that the temperature of the heat exchange medium rises from the entrance into the temperature zone to the exit from the temperature zone by from 0 to 15° C. In other words, the aforementioned $\Delta T$ may, in accordance with the invention, be from 1 to 10° C., or from 2 to 8° C., or from 3 to 6° C.

The entrance temperatures of the heat exchange media in temperature zones A, B of the two-zone tube bundle reactors in an acrolein partial oxidation to acrylic acid are to be selected in accordance with the invention such that they correspond to the temperatures and temperature differences $\Delta T^{BA}$ required for temperature zones A, B in this document for this reaction. In inventive long-term operation, they are to be changed in accordance with the invention.

It should be pointed out once again here that, for a performance of an inventive partial oxidation of acrolein to acrylic acid, it is also possible in particular to use the two-zone tube bundle reactor type which is described in DE-B 22 01 528 and includes the possibility of removing a portion of the hot heat exchange medium of temperature zone B to temperature zone A, in order if appropriate to heat a reaction gas input mixture 2 which is too cold or a cold cycle gas. The tube bundle characteristics within an individual reaction zone may also be configured as described in EP-A 382 098.

It is of course also possible to carry out an inventive two-stage partial oxidation of propylene to acrylic acid by combining two two-zone tube bundle reactors to give a four-zone tube bundle reactor, as described in WO 01/36364. In these cases, there is normally an inert bed between fixed bed catalyst charge 1 and fixed bed catalyst charge 2. However, such an intermediate inert bed may also be dispensed with. The length of the reaction tubes in the event of combination corresponds in many cases to the sum of the lengths of the uncombined tube bundle reactors.

Generally, it is favorable to operate an inventive partial oxidation of propylene to acrolein such that the propylene content in the product gas mixture of this partial oxidation does not exceed the value of 10 000 ppm by weight, preferably 6000 ppm by weight and more preferably from 4000 to 2000 ppm by weight.

Generally, it is favorable to operate an inventive partial oxidation of acrolein to acrylic acid such that the acrolein content in the product gas mixture of this partial oxidation does not exceed the value of 1500 ppm by weight, preferably 600 ppm by weight and more preferably 350 ppm by weight.

The propene content in starting reaction gas mixture 1 in the process according to the invention may, for example, be at values of from 3 to 25% by volume, often from 4 to 20% by volume, or from 5 to 15% by volume, frequently from 6 to 12% by volume or from 6 to 8% by volume (based in each case on the total volume). Suitable propylene sources are in particular "polymer-grade propylene" and "chemical-grade propylene" according to WO 2004/009525.

Frequently, the propylene→acrolein process according to the invention will be carried out at a propene: oxygen: inert gases (including steam) volume ratio in starting reaction gas mixture 1 of 1:(1.0 to 3.0):(5 to 25), preferably 1:(1.7 to 2.3):(10 to 15). In general, the inert gas will consist to an extent of at least 20% of its volume of molecular nitrogen. However, it may also consist to an extent of ≧30% by volume, or to an extent of ≧40% by volume, or to an extent of ≧50% by volume, or to an extent of ≧60% by volume, or to an extent of ≧70% by volume, or to an extent of ≧80% by volume, or to an extent of ≧90% by volume, or to an extent of ≧95% by volume of molecular nitrogen (possible inert gases, in addition to molecular nitrogen, are, for example, gases such as propane, ethane, methane, pentane, butane, $CO_2$, CO, steam and/or noble gases). Of course, the inert diluent gas in an inventive propylene partial oxidation to acrolein may also consist to an extent of up to 50 mol %, or up to 75 mol % and more of propane. Cycle gas, as remains in the two-stage propylene partial oxidation to acrylic acid after removal of the acrylic acid from the product gas mixture may also be part of the diluent gas.

The aforementioned composition ranges also apply to such two-stage processes, both in cases of secondary gas supply and in cases where no secondary gas is supplied.

Starting reaction gas mixtures 1 suitable in accordance with the invention are, for example, those which are composed of

| | |
|---|---|
| from 6 to 15% (preferably 7 to 11%) by volume | of propene, |
| from 4 to 20% (preferably 6 to 12%) by volume | of water, |
| from ≧0 to 10% (preferably ≧0 to 5%) by volume | of constituents other than propene, water, oxygen and nitrogen, | sufficient molecular oxygen that the molar ratio of molecular oxygen present to propene present is from 1.5 to 2.5 (preferably from 1.6 to 2.2), and, as the remainder up to 100% by volume of the total amount, of molecular nitrogen, as recommended by DE-A 10302715.

Especially at high propene or acrolein loadings of the particular fixed bed catalyst charge, the additional use of inert diluent gases with high specific heat is recommended.

The acrolein content in starting reaction gas mixture 2 may, in accordance with the invention, for example, be at values of from 3 to 25% by volume, often from 4 to 20% by volume, or from 5 to 15% by volume, frequently at from 4 to 10% by volume or from 5 to 8% by volume (based in each case on the total volume).

Frequently, the process according to the invention will be performed with an acrolein:oxygen:steam:inert gas volume ratio (l (STP)) present in reaction gas input mixture 2 of 1:(1 to 3):(0 to 20):(3 to 30), preferably of 1:(1 to 3):(0.5 to 10):(7 to 10).

Of course, the process according to the invention can also be performed with an acrolein:oxygen:steam:others volume ratio (l (STP)) present in reaction gas input mixture 2 of 1:(0.9 to 1.3):(2.5 to 3.5):(10 to 12).

At this point, it should be emphasized that favorable active compositions both for the fixed bed catalyst charge 1 and for the fixed bed catalyst charge 2 are also the multimetal oxide compositions of DE-A 10261186.

Especially in the case of a two-stage inventive heterogeneously catalyzed gas phase partial oxidation of propylene to acrylic acid, the following conditions of the reaction gas input mixture are also useful.

For example, reaction gas input mixture 1 may comprise ≧0.01% by volume, or ≧0.1% by volume, or ≧0.5% by volume, or ≧2% by volume of $CO_2$. Usually, the aforementioned $CO_2$ content will be ≦25% by volume.

Especially when the source used for the molecular oxygen in the process according to the invention is air, reaction gas input mixture 1 will comprise molecular nitrogen as a further inert diluent gas. In principle, reaction gas input mixture 1 in the process according to the invention may comprise ≧1% by volume, or ≧5% by volume, or ≧10% by volume, or ≧20% by volume, or ≧30% by volume, or ≧40% by volume of molecular nitrogen. However, the content in reaction gas input mixture 1 of molecular nitrogen will generally be at values of ≦80 mol %, or ≦70 mol %, or ≦60 mol %.

Reaction gas input mixture 1 may also (as already stated) comprise propane as an inert diluent gas. This propane content of reaction gas input mixture 1 may be up to 70% by volume (for example from 5 to 70% by volume), or up to 60% by volume, or up to 50% by volume, or up to 40% by volume, or to 30% by volume, or to 20% by volume, or up to 10% by volume. Frequently, this propane content will be ≧0.5 or ≧1% by volume. However, it may also be at values of ≧0.01% by volume, or ≧0.02% by volume, or ≧0.03% by volume. In general, reaction gas input mixture 1 comprises ≦10% by volume, in many cases ≦5% by volume of propane.

In the process according to the invention, this propane may be added, for example, deliberately as an inert diluent gas to be supplied separately to reaction gas input mixture 1.

However, it will be appreciated that the propane may also be part of reaction gas input mixture 1 by virtue of a partial dehydrogenation or oxidehydrogenation of propane functioning as the propylene source therefor (generally, these are effected under heterogeneous catalysis). In other words, the propylene present in reaction gas input mixture 1 may be supplied to reaction gas input mixture 1 at least partly with accompaniment by unconverted propane from a partial dehydrogenation (for example homogeneously and/or heterogeneously catalyzed, in the presence and/or with exclusion of molecular oxygen).

The process according to the invention comprises in particular also those embodiments in which reaction gas input mixture 1 comprises from >0 to 35% by volume, frequently from 1 to 25% by volume, or from 5 to 15% by volume, or to 10% by volume of $H_2O$.

Typical reaction gas input mixtures 1 are, for example, those which comprise:

| | |
|---|---|
| from 5 or 6 to 11% by volume | of propene, |
| from 2 or 6 to 12% by volume | of water, |
| from >0, frequently ≧0.5 or ≧1 to 10% by volume | of propane, |
| from ≧0 to 5% by volume | of constituents other than propene, propane, water, oxygen and nitrogen, sufficient molecular oxygen that $V_1$ is from 1 to 3, and, as the remainder up to 100% by volume of the total amount, molecular nitrogen. |

Inventive reaction gas input mixtures 1 may also comprise:

| | |
|---|---|
| from 6 to 9% by volume | of propylene, |
| from 8 to 18% by volume | of molecular oxygen, |
| from 6 to 30 or to 35% by volume | of propane and |
| from 32 to 72% by volume | of molecular nitrogen. |

Inventive reaction gas input mixtures 2 may, for example, comprise:

| | |
|---|---|
| from 4.5 to 8% by volume | of acrolein, |
| from 2.25 to 9% by volume | of molecular oxygen, |
| from 6 to 30 or to 35% by volume | of propane, |
| from 32 to 72% by volume | of molecular nitrogen, |
| from 5 to 30% by volume | of steam. |

Inventive reaction gas input mixtures 1 may also comprise up to 20% by volume of $H_2$.

In other words, reaction gas input mixtures 1 of the process according to the invention may also comprise:

| | |
|---|---|
| from 4 to 25% by volume | of propylene, |
| from 6 to 70% by volume | of propane, |
| from 5 to 60% by volume | of $H_2O$, |
| from 8 to 65% by volume | of $O_2$ and |
| from 0.3 to 20% by volume | of $H_2$. |

However, the process according to the invention is also favorable when reaction gas input mixture 1 comprises from 0.1 to 30% by volume of $CO_2$.

Reaction gas input mixtures 2 possible in accordance with the invention may also comprise:

| | |
|---|---|
| from 3 to 25% by volume | of acrolein, |
| from 5 to 65% by volume | of molecular oxygen, |
| from 6 to 70% by volume | of propane, |
| from 0.3 to 20% by volume | of molecular hydrogen and |
| from 8 to 65% by volume | of steam. |

It is essential to the invention that, for all aforementioned cases, the process according to the invention can be employed for both stages in each case both when the two stages are operated independently of one another and when they are operated in series connection as detailed above.

At this point, it should be mentioned once again that especially a portion of reaction gas input mixture 1 may be so-called cycle gas. This is gas which remains, for example, in an inventive two-stage partial oxidation of propylene to acrylic acid after the product removal (acrylic acid removal) from the product gas mixture of the second stage, and, in the case of a series connection of the two stages, is generally partly recycled as inert diluent gas to charge the first and/or second stage.

A typical cycle gas composition is:

| | |
|---|---|
| 0-0.1% | by volume of others, for example diphenyl, diphenyl ether and/or dimethyl phthalate, |
| 0-0.1% | by volume of acrylic acid, |
| 0-0.1% | by volume of acrolein, |
| 3-5% | by volume of oxygen, |
| 1-5% | by volume of steam, |
| 0-3% | by volume of carbon monoxide, |
| 0-8% | by volume of carbon dioxide, |
| 0-2% | by volume of propane, |
| 0.1-0.5% | by volume of propylene, |
| 85-95% | by volume of nitrogen. |

The acrylic acid can be removed, for example, as described in EP-A 982 287, EP-A 982 289, DE-A 199 24 532, DE-A 101 15 277, DE-A 196 06 877, DE-A 197 40 252, DE-A 196 27 847, DE-A 100 53 086, EP-A 982 288 and DE-A 196 27 847.

Designs of a two-zone tube bundle reactor favorable in accordance with the invention for an inventive heterogeneously catalyzed partial gas phase oxidation of propylene to acrolein (for example as the first stage of a two-stage acrylic acid preparation process) may have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst Tubes:

| | |
|---|---|
| material of the catalyst tubes: | ferritic steel; |
| dimensions of the catalyst tubes: | length, for example, 3500 mm; external diameter, for example, 30 mm; wall thickness, for example, 2 mm; | number of catalyst tubes in the tube bundle: for example, 30 000, or 28 000, or 32 000, or 34 000, or 36 000, or 40 000; in addition up to 10 thermal tubes (as described in EP-A 873 783 and EP-A 12 70 065) which are charged in the same way as the catalyst tubes (in a spiral manner rotating from the very outside inward), for example of the same length and wall thickness but having an external diameter of, for example, 33.4 mm and a centered thermowell of external diameter, for example, 8 mm and wall thickness of, for example, 1 mm; reactor (same material as the catalyst tubes):
cylindrical vessel of internal diameter 6000-8000 mm or to 10 000 mm;
reactor hoods plated with type 1.4541 stainless steel; plating thickness: a few mm;
annularly arranged tube bundle, for example with a free central space:
diameter of the free central space: for example, 1000-2500 mm (for example 1200 mm, or 1400 mm, or 1600 mm, or 1800 mm, or 2000 mm, or 2200 mm, or 2400 mm);
normally homogeneous catalyst tube pitch in the tube bundle (6 equidistant adjacent tubes per catalyst tube), arrangement in an equilateral triangle, catalyst tube pitch (separation of the central internal axes of immediately adjacent catalyst tubes): 35-45 mm, for example 36 mm, or 38 mm, or 40 mm, or 42 mm, or 44 mm;
the catalyst tubes are secured and sealed by their ends in catalyst tube plates (upper plate and lower plate each having a thickness, for example, of 100-200 mm) and open at their upper ends into a hood joined to the vessel which has an inlet for reaction gas input mixture 1; a separating plate of thickness 20-100 mm disposed, for example, at half the catalyst tube length, divides the reactor space symmetrically into two temperature zones A (upper zone) and B (lower zone); each temperature zone is divided into 2 equidistant longitudinal sections by a deflecting plate;
the deflecting plate preferably has annular geometry; the catalyst tubes are advantageously secured and sealed at the separating plate; they are not secured and sealed at the deflecting plates, so that the transverse flow rate of the salt melt within one zone is very substantially constant;
each zone is provided with salt melt as a heat carrier by a dedicated salt pump; the feed of the salt melt is, for example, below the deflecting plate and the withdrawal is, for example, above the deflecting plate;
a substream is, for example, removed from both salt melt circuits and cooled, for example, in one common or two separate indirect heat exchangers (steam-raising);
in the first case, the cooled salt melt stream is divided, combined with the particular residual stream and pressurized into the reactor by the particular pump into the appropriate annular channel which divides the salt melt over the circumference of the vessel;
the salt melt reaches the tube bundle through the window disposed in the reactor jacket; the flow is, for example, in a radial direction to the tube bundle;
in each zone, the salt melt flows around the catalyst tubes as dictated by the deflection plate, for example in the sequence
    from the outside inward,
    from the inside outward;
through windows mounted around the circumference of the vessel, the salt melt collects at the end of each zone in an annular channel disposed around the reactor jacket, in order to be pumped in a circuit including substream cooling;
the salt melt is conducted from bottom to top through each temperature zone.
The reaction gas mixture leaves the reactor of the first stage at a temperature a few degrees higher than the corresponding salt bath entrance temperature of the first reactor. For further processing, the reaction gas mixture is appropriately cooled to from 220° C. to 280° C., preferably from 240° C. to 260° C., in a separate aftercooler which is connected downstream of the reactor of the 1st stage.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.
Salt Melt:
The salt melt used may be a mixture of 53% by weight of potassium nitrate, 40% by weight of sodium nitrite and 7% by weight of sodium nitrate; both reaction zones and the aftercooler advantageously employ a salt melt of the same composition; the amount of salt pumped by circulation in the reaction zones may be approx. 10 000 m³/h per zone. The salt melts of the two temperature zones may each be cooled by appropriate salt melt withdrawal in a separate salt bath cooler or else in a common salt bath cooler.
Flow Control:
Reaction gas input mixture 1 advantageously flows from top to bottom through the first stage reactor, while the salt melts having different temperatures of the individual zones are advantageously conveyed from bottom to top;
Catalyst tube and thermal tube charge (from top to bottom), for example:
Section 1: length 50 cm
    steatite rings of geometry 7 mm×7 mm×4 mm (external diameter×length×internal diameter) as a preliminary bed. Alternatively, it is also possible here to use steatite rings of geometry 7 mm×3 mm×4 mm as a preliminary bed.
Section 2: length 140 cm
    catalyst charge of a homogeneous mixture of 30% by weight of steatite rings of geometry 5 mm×3 mm×2 mm (external diameter×length×internal diameter) and 70% by weight of unsupported catalyst from section 3.
Section 3: length 160 cm
    catalyst charge of annular (5 mm×3 mm×2 mm=external diameter×length×internal diameter) unsupported catalyst according to example 1 of DE-A 10046957 (stoichiometry: $[Bi_2W_2O_9.3WO_3]_{0.5}[Mo_{12}Co_{5.5}Fe_{2.94}Si_{1.59}K_{0.08}O_x]_1$).
(Alternatively, the sections 1 to 3 thus charged may also have the following lengths:
section 1: 50 cm;
section 2: 100 cm; and
section 3: 200 cm.
This length distribution is favorable in the case of additional use of, for example, up to 50% by volume of propane as an inert diluent gas.)

Configurations of a two-zone tube bundle reactor favorable in accordance with the invention for an inventive heterogeneously catalyzed partial gas phase oxidation of acrolein to acrylic acid (for example as the second stage of a two-stage partial oxidation of propylene to acrylic acid) can be designed as follows:

Everything as in the two-zone tube bundle reactor for the first reaction stage. However, the thickness of the upper and lower catalyst tube plates is frequently 100-200 mm, for example 110 mm, or 130 mm, or 150 mm, or 170 mm, or 190 mm (in general, the first-stage reactor and the second-stage reactor in the two-stage process have the same number of catalyst tubes).

The aftercooler is dispensed with; instead, the lower openings of the catalyst tubes open into a hood which is connected to the vessel at the lower end and has an outlet for the product gas mixture; the upper temperature zone is zone A and the lower temperature zone is temperature zone B. Between the "aftercooler" outlet and the "reactor for the second reaction stage" inlet there is appropriately a supply means for compressed air.

The catalyst tube and thermal tube charge (from top to bottom) may, for example, be as follows:

Section 1: length 20 cm
  steatite rings of geometry 7 mm×7 mm×4 mm (external diameter×length×internal diameter) as a preliminary bed. Alternatively, it is also possible here to use steatite rings of geometry 7 mm×3 mm×4 mm as a preliminary bed.

Section 2: length 90 cm
  catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm
  catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm
  catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

The second stage catalyst tube and thermal tube charge may also have the following appearance (from top to bottom):

Section 1: length 20 cm
  steatite rings of geometry 7 mm×7 mm×4 mm (external diameter×length×internal diameter) as a preliminary bed. Alternatively, it is also possible here to use steatite rings of geometry 7 mm×3 mm×4 mm as a preliminary bed.

Section 2: length 140 cm
  catalyst charge of a homogeneous mixture of 25% by weight of steatite rings of geometry 7 mm×3 mm×4 mm (external diameter×length×internal diameter) and 75% by weight of coated catalyst from section 3.

Section 3: length 190 cm
  catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

When, for example, up to 50% by volume of propane is used additionally as an inert diluent gas, the second-stage catalyst tube and thermal tube charge (from top to bottom and with use of the same coated catalyst) may appropriately have the following appearance:

Section 1: length 20 cm
  steatite rings of geometry 7 mm×7 mm×4 mm (or alternatively 7 mm×3 mm×4 mm) (in each case external diameter×length×internal diameter) as a preliminary bed.

Section 2: length 130 cm
  catalyst charge of a homogeneous mixture of 30% by weight of steatite rings of geometry 7 mm×3 mm×4 mm (external diameter×length×internal diameter) and 70% by weight of coated catalyst from section 3.

Section 3: length 200 cm
  catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

In the first-stage charges mentioned, the unsupported catalyst from example 1 of DE-A 100 46 957 may also be replaced by:
a) a catalyst according to example 1c of EP-A 15 565 or a catalyst to be prepared in accordance with this example, except having the active composition $Mo_{12}Ni_{6.5}Zn_2Fe_2Bi_1P_{0.0065}K_{0.06}O_x \cdot 10SiO_2$;
b) example no. 3 of DE-A 19855913 as an unsupported hollow cylinder catalyst of geometry 5 mm×3 mm×2 mm or 5 mm×2 mm×2 mm;
c) unsupported multimetal oxide II catalyst according to example 1 of DE-A 19746210;
d) one of the coated catalysts 1, 2 and 3 of DE-A 10063162, except applied in the same coating thickness to support rings of geometry 5 mm×3 mm×1.5 mm or 7 mm×3 mm×1.5 mm.

In all of the abovementioned second-stage charges, the coated catalyst according to preparative example 5 of DE-A 10046928 may be replaced by:
a) coated catalyst S1 or S7 from DE-A 44 42 346 having an active composition content of 27% by weight and a coating thickness of 230 μm;
b) a coated catalyst according to examples 1 to 5 of DE-A 198 15 281, except applied to support rings of geometry 7 mm×3 mm×4 mm having an active composition content of 20% by weight;
c) coated catalyst having biphasic active composition of stoichiometry $(Mo_{10.4}V_3W_{1.2}O_x)(CuMo_{0.5}W_{0.5}O_4)_{1.6}$, prepared according to DE-A 197 36 105 and having an active composition content of 20% by weight, applied to the aforementioned 7 mm×3 mm×4 mm support.

According to the invention, fixed bed catalyst charge 1 and fixed bed catalyst charge 2 (and also the remaining process conditions (for example intermediate regeneration)) are appropriately otherwise selected (for example by dilution with, for example, inert material, additional use of inert gas) in such a way that the temperature difference between the hotspot maximum of the reaction gas mixture in the individual temperature zones and the particular temperature of the temperature zone, even in long-term operation, generally does not exceed 80° C. This temperature difference is usually ≦70° C., frequently from 20 to 70° C. or to 50° C.; this temperature difference is preferably small even in long-term operation. For safety reasons, fixed bed catalyst charges 1 and 2 and the other process conditions are also selected in a manner known per se to those skilled in the art (for example by dilution with, for example, inert material) in such a way that the peak-to-salt-temperature sensitivity (the change of $\Delta T^{HB}_A$ or $\Delta T^{HB}_B$ on increase of the temperature of the accompanying temperature zone by 1° C.) (cf. definition in EP-A 1106598), especially also in long-term operation, is ≦9° C., or ≦7° C., or ≦5° C., or ≦3° C. The aforementioned applies thus quite generally for the inventive long-term operation of a heterogeneously catalyzed partial gas phase oxidation of an organic starting compound.

Aftercooler and reactor for the second stage are connected by a connecting tube whose length is less than 25 m.

In the aforementioned reactor arrangement, the annular shaped diluent bodies and the annular shaped catalyst bodies in the second reaction stage may also be replaced by spherical shaped diluent bodies and spherical shaped catalyst bodies (each having a radius from 2 to 5 mm and having an active composition content of from 10 to 30% by weight, frequently from 10 to 20% by weight). This also applies for the examples and comparative examples which follow.

EXAMPLES AND COMPARATIVE EXAMPLES

A reaction tube (V2A steel; external diameter 33.7 mm, wall thickness 2 mm, internal diameter 29.7 mm, length: 350 cm, and also a thermal tube (external diameter 10 mm) centered in the middle of the reaction tube for a accommodating a thermoelement with which the temperature in the reaction tube can be determined over its entire length) was charged freshly from top to bottom as follows:

Section 1: length 20 cm steatite rings of geometry 7 mm×3 mm×4 mm (external diameter×length×internal diameter) as a preliminary bed.

Section 2: length 90 cm catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

From top to bottom, the first 175 cm were thermostated by means of a salt bath A pumped in countercurrent which was supplied with the temperature $T^A$. The second 175 cm were thermostated by means of a salt bath B pumped in countercurrent which was supplied with the temperature $T^B$.

Gas Phase Oxidation:

The above-described reaction tube was charged continuously with a reaction gas input mixture of the following composition:

4.7% by volume of acrolein, 0.4% by volume of acrylic acid, 0.3% by volume of propene, 4.7% by volume of molecular oxygen, 0.6% by volume of CO, 1.1% by volume of $CO_2$, 8.1% by volume of water and 80% by volume of nitrogen.

The reaction gas mixture flowed through the reaction tube from top to bottom.

The pressure at the inlet of the reaction tube was 2.0 atm. The loading of the fixed catalyst bed with acrolein was 140 l (STP)/l·h.

The temperatures $T^A$, $T^B$ were each adjusted such that, based on single pass of the reaction gas mixture through the reaction tube, a conversion $C^B_{AC}$ of acrolein of 99.5 mol % always resulted. An intermediate regeneration of the fixed catalyst bed was disregarded. The table which follows indicates the selectivity of acrylic acid formation $S^{AA}$ (based on single pass) achieved as a function of $T^A$, $T^B$ in the long-term operation of the reaction tube. The operating times of the fixed catalyst bed reported are based on the time of completion of conditioning of the fixed catalyst bed as the zero point (operation of the "freshly" charged fixed catalyst bed). In operation of the freshly conditioned fixed catalyst bed, $T^{maxA}$ and $T^{maxB}$ were 305° C. ($T^{maxA}$) and 297° C. ($T^{maxB}$). The table also comprises the values for $T^{maxA}$ and $T^{maxB}$ resulting at later stages.

TABLE

| Operating time | $T^A$ | $T^B$ | $T^{maxA}$ | $T^{maxB}$ | $S^{AA}$ (mol %) |
|---|---|---|---|---|---|
| 0 | 271 | 282 | 305 | 297 | 94.7 |
| 2 months | 271 | 281 | 305 | 297 | 94.8 |
| 4 months | 272 | 279 | 304 | 295 | 94.8 |
| 6 months | 275 | 279 | 308 | 298 | 94.8 |
| 10 months | 276 | 279 | 308 | 300 | 94.8 |

When $T^A$ was adjusted to 273° C. and $T^B$ to 284° C. after 10 months of operating time, it was likewise possible to achieve a $C^B_{AC}$ of 99.5 mol % (based on single pass), but $S^{AA}$ was only 94.1 mol %. $T^{maxA}$ in this case was 296° C. and $T^{maxB}$ was 315° C.

U.S. Provisional Patent Application No. 60/759,557, filed on Jan. 18, 2006, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

What is claimed is:

1. A process for the long-term operation of a heterogeneously catalyzed partial gas phase oxidation of an organic starting compound to an organic target compound, in which a reaction gas input mixture comprising the organic starting compound and molecular oxygen is first conducted through a freshly charged fixed catalyst bed which is installed into two spatially successive temperature zones A, B whose temperatures $T^A$ and $T^B$ are such that the difference $\Delta T^{BA}$ between the temperature $T^B$ of the temperature zone B and the temperature $T^A$ of the temperature zone A and calculated with the higher of the two temperatures as the minuend is >0° C., with the proviso that the reaction gas input mixture flows through temperature zones A, B in the time sequence "first A" and "then B", temperature zone A extending up to a conversion of the organic starting compound of $C^A$=from 15 to 85 mol % and the conversion of the organic starting compound increasing in temperature zone B to a value $C^B$ of ≧90 mol %, and in which, with increasing operating time, in order to counteract the reduction in the quality of the fixed catalyst bed, the temperature of temperature zones A, B is then changed, wherein, with increasing operating time, the temperature of that temperature zone which initially had the lower temperature is increased and the difference $\Delta T^{BA}$ between the temperatures of the two temperature zones is reduced, the difference being formed by the temperature of that temperature zone which initially had the higher temperature retaining its position as the minuend, wherein $\Delta T^{BA}$ does not change its preceding sign for a minimum of 2 months operating time.

2. The process according to claim 1, wherein the partial gas phase oxidation is that of propylene to acrolein and/or acrylic acid, or that of isobutene to methacrolein and/or methacrylic acid, or that of acrolein to acrylic acid, or that of methacrolein to methacrylic acid, or that of propane to acrylic acid, or that of isobutane to methacrylic acid.

3. The process according to claim 1, wherein the organic starting compound comprises at least one of propylene, acrolein, 1-butene, 2-butene, ethane, benzene, m-xylene, p-xylene, isobutane, isobutene, tert-butanol, isobutyraldehyde, methyl ether of tert-butanol, o-xylene, naphtalene, butadiene, ethylene, propane and methacrolein.

4. The process according to claim 1, wherein the gas phase oxidation is the partial oxidation of acrolein to acrylic acid in a two-stage gas phase partial oxidation of propylene to acrylic acid.

5. The process as claimed in claim 1, wherein temperature zone A had the initially lower temperature.

6. The process according to claim 5, wherein the temperature of temperature zone B is reduced with increasing operating time.

7. The process according to claim 5, wherein the temperature of temperature zone B is increased with increasing operating time.

8. The process according to claim 1, wherein $\Delta T^{BA}$ does not change its preceding sign for a minimum of 12 months operating time.

9. The process according to claim 1, wherein the magnitude of $\Delta T^{BA}$ does not exceed 50° C.

10. The process according to claim 1, wherein the difference between the maximum reaction temperature in temperature zone A, $T^{maxA}$, and the maximum reaction temperature in temperature zone B, $T^{maxB}$, formed as $T^{maxA} - T^{maxB}$, is $\geq 0°$ C. both at the start of the process and in long-term operation.

11. The process according to claim 1, which is a partial oxidation of acrolein to acrylic acid, and $C^A$ is from 40 to 85 mol %.

12. The process according to claim 1, which is a partial oxidation of acrolein to acrylic acid, and both the temperature of temperature zone A and of temperature zone B in long-term operation is from 230 to 340° C.

13. The process according to claim 1, which is a partial oxidation of acrolein to acrylic acid, and the loading of the fixed catalyst bed with acrolein is from 90 to 300 (STP)/l·h.

14. The process according to claim 1, which is a partial oxidation of acrolein to acrylic acid, and the difference between the maximum reaction temperature in temperature zone A, $T^{maxA}$, and the maximum reaction temperature in temperature zone B, $T^{maxB}$, formed as $T^{maxA} - T^{maxB}$, is from 0 to 15° C. both at the start of the process and in long-term operation.

15. The process according to claim 1, which is a partial oxidation of propylene to acrolein and $C^A$ is from 30 to 80 mol %.

16. The process according to claim 1, which is a partial oxidation of propylene to acrolein, and both the temperature of temperature zone A and of temperature zone B in long-term operation is from 290 to 380° C.

17. The process according to claim 1, which is a partial oxidation of propylene to acrolein, and the loading of the fixed catalyst bed with propylene is from 120 to 300 (STP)/l·h.

18. The process according to claim 1, which is carried out in a multiple catalyst tube fixed bed reactor.

19. The process according to claim 1, wherein $\Delta T^{BA}$ does not change its preceding sign for a minimum of 18 months operating time.

20. The process according to claim 1, wherein $\Delta T^{BA}$ does not change its preceding sign for a minimum of 24 months operating time.

21. The process according to claim 1, wherein $\Delta T^{BA}$ does not change its preceding sign for a minimum of 30 months operating time.

22. The process according to claim 1, wherein $\Delta T^{BA}$ does not change its preceding sign for a minimum of 36 months operating time.

* * * * *